(12) United States Patent
Cellier et al.

(10) Patent No.: US 7,202,367 B2
(45) Date of Patent: Apr. 10, 2007

(54) PROCESS FOR ARYLATING OR VINYLATING OR ALKYNATING A NUCLEOPHILIC COMPOUND

(75) Inventors: Pascal Philippe Cellier, L'escale (FR); Henri-Jean Cristau, St Aunes (FR); Jean-Francis Spindler, Lyons (FR); Marc Taillefer, Vailhauques (FR)

(73) Assignee: Rhodia Chimie, Aubervilliers (FR)

( * ) Notice: Subject to any disclaimer, the term of this patent is extended or adjusted under 35 U.S.C. 154(b) by 574 days.

(21) Appl. No.: 10/159,829

(22) Filed: May 31, 2002

(65) Prior Publication Data

US 2003/0236413 A1   Dec. 25, 2003

(51) Int. Cl.
C07D 249/02 (2006.01)
C07D 233/04 (2006.01)
C07D 233/54 (2006.01)
C07D 235/04 (2006.01)
C07D 257/04 (2006.01)

(52) U.S. Cl. .............. 548/265.8; 548/265.8; 548/371.1; 548/577

(58) Field of Classification Search ......... 548/371.1, 548/577, 265.8; 514/383, 406, 429
See application file for complete search history.

(56) References Cited

OTHER PUBLICATIONS

Buchwald et al, "A General and Efficient Copper Catalyst for the Amidation of Aryl Halides and the N-arylation of Nitrogen Heterocycles." Journal of the Americal Chemical Society (2001), vol. 123. pp. 7727-7729.*
U.S. Appl. No. 10/128,981, Buchwald et al., filed Apr. 24, 2002.*

* cited by examiner

Primary Examiner—Joseph K. McKane
Assistant Examiner—Janet L. Coppins

(57) ABSTRACT

The present invention concerns a process for arylating or vinylating or alkynating a nucleophilic compound. More particularly, the invention concerns arylating nitrogen-containing organic derivatives. The arylating or vinylating or alkynating process of the invention consists of reacting a nucleophilic compound with a compound carrying a leaving group and is characterized in that the reaction is carried out in the presence of an effective quantity of a catalyst based on a metallic element M selected from groups (VIII), (Ib) and (IIb) of the periodic table and at least one ligand comprising at least one imine function and at least one supplemental nitrogen atom as the chelating atoms.

30 Claims, No Drawings

PROCESS FOR ARYLATING OR VINYLATING OR ALKYNATING A NUCLEOPHILIC COMPOUND

The present invention relates to a process for arylating or vinylating or alkynating a nucleophilic compound.

More particularly, the invention relates to arylating nitrogen-containing organic derivatives.

Many important compounds exist in the agrochemical and pharmaceutical fields, for example arylhydrazines, which result from arylating a nucleophilic compound by creating a carbon-nitrogen bond.

A conventional arylation method consists of carrying out the Ullmann reaction (Ullmann F. and Kipper H., Ber. Dtsch. Chem. Ges. 1905, 38, 2120–2126), by prolonged heating of the reagents at high temperature, in the presence of catalytic or stoichiometric copper. The reactions are usually limited to using aryl iodides and their yields are reduced by competitive formation of biaryl homocoupling products.

Arylation reactions require a catalyst; a number of types of catalyst have been described.

Palladium was used by Buchwald et al., in particular to carry out indole arylation (Org. Lett. 2000, 2, 1403–1406), in the presence of a base in toluene at 80° C.–100° C. Generally, the yields are satisfactory, but the reaction temperature is still high for this type of palladium-based catalyst.

Copper has also been used (Chiriac et al., Rev. Roum. Chim. 1969, 14, 1263–1267) to carry out arylation of sodium salts and pyrazoles by iodobenzene in the presence of a catalytic quantity of copper under DMF reflux. The conditions described are very severe, the temperature is 153° C. and the reaction period is very long at 30 to 40 hours.

Beletskaya et al. (Tetrahedron Lett. 1998, 39, 5617–5622) proposed a combination of palladium and copper when N-arylating benzotriazole. The presence of copper is indispensable to controlling the selectivity of the reaction. The catalyst is a phase transfer catalyst which is not easy to use on an industrial scale.

International patent WO-A-98/00399 proposes the use of a nickel catalyst, but this has proved to be of little effect when arylating heterocycles such as imidazole.

Chan et al. also described (J. Chem. RES. (S) 2000, 367–369) the arylation of azoles from diaryliodonium salts in the presence of a cobalt catalyst under phase transfer conditions.

Buchwald et al. (J. Am. Chem. Soc. 2001, 123, 7727–7729) recently developed a method for arylating nitrogen-containing nucleophiles catalysed by copper. Its catalytic system, composed of a catalyst that is insensitive to air, cuprous iodide and the trans-1,2-diaminocyclohexane ligand, allows heterocycles such as pyrazoles, indoles, carbazole, pyrrole, indazole, imidazole, phthalazinone and 7-azaindole to be arylated in dioxane at 110° C.

The disadvantage of that process is that the temperature is still high when arylation is carried out by aryl chlorides or even by aryl iodides.

The present invention aims to provide a process that overcomes the disadvantages cited above and which is applicable to a very large number of nucleophiles.

We have now discovered, and this constitutes the subject matter of the present invention, a process for arylating or vinylating or alkynating a nucleophilic compound, consisting of reacting said compound with a compound carrying a leaving group, characterized in that the reaction is carried out in the presence of an effective quantity of a catalyst based on a metallic element M selected from groups (VIII), (Ib) and (IIb) of the periodic table and at least one ligand comprising at least one imine function and at least one supplemental nitrogen atom as chelating atoms.

Throughout the description of the present invention, the term "arylation" is used in its broad sense since it is envisaged that the compound employed carries a leaving group which is either of the unsaturated aliphatic type, or of the carbocyclic aromatic or heterocyclic type.

The term "nucleophilic compound" means an organic hydrocarbon compound that may be acyclic or cyclic and comprises at least one atom carrying a free electron pair which may or may not carry a charge, preferably a nitrogen, oxygen, sulphur, phosphorus or carbon atom.

The term "imine function" means a functional group comprising a nitrogen atom bonded to a carbon atom via a double bond.

The term "other supplemental nitrogen atom" means a nitrogen atom that can be carried by a further imine function and/or by a functional group such as an amine, amide, urea, nitrile, guanidine, sulphonamide, phosphinamide group and/or a nitrogen atom carrying a free electron pair included in a saturated, unsaturated or aromatic cycle.

As mentioned above, the nucleophilic compound comprises at least one atom carrying a free electron pair, which can be carried by a functional group.

Examples of functional groups comprising said atoms that can be mentioned are:

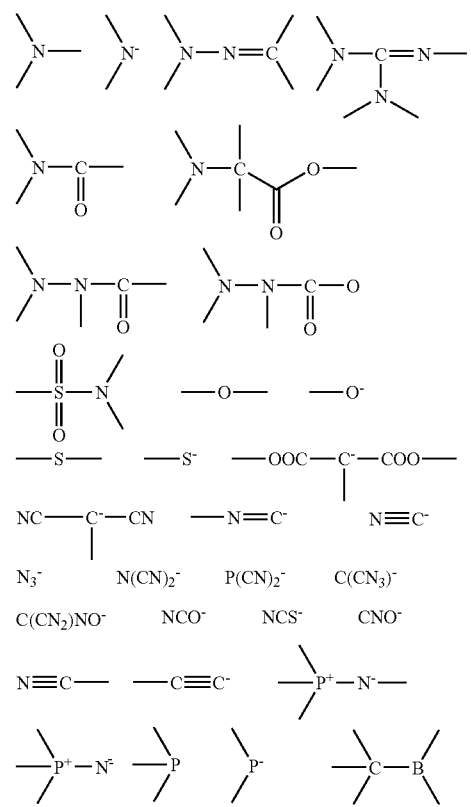

In a further variation of the invention, the nucleophilic compound comprises at least one nitrogen atom carrying a free electron pair included in a saturated, unsaturated or aromatic cycle; the cycle generally contains 3 to 8 atoms.

It should be noted that when the nucleophilic compound comprises a functional group, examples of which were given above, which carries one or more negative charges, said compound is then in its salt form. The counter-ion is generally a metallic cation such as an alkali metal, preferably sodium or lithium, or an alkaline-earth metal, preferably calcium, or the residue of an organometallic compound such as a magnesium or zinc compound.

A first advantage of the process of the invention is that it is carried out at moderate temperatures.

A further advantage is that a wide range of arylation agents for nucleophiles can be used, not only aryl iodides, but also aryl bromides.

A still further advantage of the process of the invention is the possibility of using copper rather than palladium as the catalyst, bringing an additional economic advantage.

In accordance with the process of the invention, the catalyst is associated with a ligand which is polydentate, at least bidentate, tridentate or even tetradentate, and which comprises the atoms defined above in the description of the invention.

A first category of ligands for carrying out the process of the invention is constituted by hydrazone type ligands, in particular those with formula:

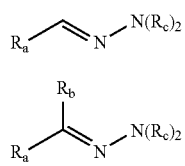

in which formulae:
one of groups $R_a$ and $R_b$ can comprise at least one nitrogen atom or a group comprising a nitrogen atom;
$R_a$ and $R_b$ independently represent a hydrocarbon group containing 1 to 20 carbon atoms, which may be a linear or branched, saturated or unsaturated, acyclic aliphatic group; a monocyclic or polycyclic, saturated, unsaturated or aromatic carbocyclic or heterocyclic group; or a concatenation of said groups;
or $R_a$ and $R_b$ can be bonded to constitute, with the carbon atoms carrying them, a monocyclic or polycyclic, saturated or unsaturated carbocyclic or heterocyclic group containing 3 to 20 atoms;
$R_c$ represents an alkyl group, preferably $C_1$ to $C_{12}$; an alkenyl or alkynyl group, preferably $C_2$ to $C_{12}$; a cycloalkyl group, preferably $C_3$ to $C_{12}$; an aryl or arylalkyl group, preferably $C_6$ to $C_{12}$, an amido group —CO—$NH_2$; an amido group substituted with one or two alkyl groups, preferably $C_1$ to $C_{12}$; and/or an alkenyl or alkynyl group, preferably $C_2$ to $C_{12}$; and/or a cycloalkyl group, preferably $C_3$ to $C_{12}$; and/or an aryl or arylalkyl group, preferably $C_6$ to $C_{12}$.

As mentioned above, at least one of groups $R_a$ and $R_b$ comprises a n atom or a group containing a nitrogen atom; examples that can be cited are groups such as amino, amido, . . . . The $NH_2$ group is preferred.

In formulae ($Ia_1$) and ($Ia_2$), the different symbols can in particular have the meanings given below.

Thus, $R_a$ and $R_b$ can independently represent a linear or branched, saturated or unsaturated, acyclic aliphatic group.

More precisely, $R_a$ and $R_b$ preferably represent a linear or branched, saturated acyclic aliphatic group, preferably $C_1$ to $C_{12}$, and more preferably $C_1$ to $C_4$.

The invention does not exclude the presence of an unsaturated bond on the hydrocarbon chain such as one or more double bonds, which may or may not be conjugated.

The hydrocarbon chain can optionally be interrupted by a heteroatom (for example oxygen, sulphur, nitrogen or phosphorus) or by a functional group provided that it does not react, in particular, a group such as —CO—.

The hydrocarbon chain can optionally carry one or more substituents (for example halogen, ester, amino or alkyl and/or arylphosphine) provided that they do not interfere.

The linear or branched, saturated or unsaturated acyclic aliphatic group can optionally carry a cyclic substituent. The term "cycle" means a saturated, unsaturated or aromatic carbocyclic or heterocyclic cycle.

The acyclic aliphatic group can be connected to the cycle via a covalent bond, a heteroatom or a functional group such as oxy, carbonyl, carboxyl, sulphonyl, etc. . . . . .

Examples of cyclic substituents that can be envisaged are cycloaliphatic, aromatic or heterocyclic substituents, in particular cycloaliphatic substituents containing 6 carbon atoms in the cycle or benzenic, said cyclic substituents themselves optionally carrying any substituent provided that they do not interfere with the reactions occurring in the process of the invention. Particular mention can be made of $C_1$ to $C_4$ alkyl or alkoxy groups.

More particular aliphatic groups carrying a cyclic substituent include cycloalkylalkyl groups, for example cyclohexylalkyl, or arylalkyl groups, preferably $C_7$ to $C_{12}$, in particular benzyl or phenylethyl.

In group formulae ($Ia_1$) and ($Ia_2$), groups $R_a$ and $R_b$ can also independently represent a carbocyclic group that is saturated or contains 1 or 2 unsaturated bonds in the cycle, generally $C_3$ to $C_8$, preferably with 6 carbon atoms in the cycle; said cycle can be substituted. A preferred example of this type of group that can be cited is cyclohexyl, optionally substituted with linear or branched alkyl groups containing 1 to 4 carbon atoms.

Groups $R_a$ and $R_b$ can independently represent an aromatic hydrocarbon group, in particular betweeic with general formula ($F_1$):

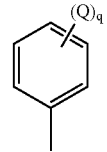

in which:
q represents a whole number from 0 to 5;
Q is a group selected from a linear or branched $C_1$ to $C_6$ alkyl group, a linear or branched $C_1$ to $C_6$ alkoxy group, a linear or branched $C_1$ to $C_6$ alkylthio group, a —$NO_2$ group, a —CN group, a halogen atom or a $CF_3$ group.
$R_a$ and $R_b$ can also independently represent a polycyclic aromatic hydrocarbon group with cycles that can between them form ortho-condensed or ortho- and peri-condensed systems. A more particular example that can be cited is a naphthyl group; said cycle can be substituted.

$R_a$ and $R_b$ can also independently represent a polycyclic hydrocarbon group constituted by at least 2 saturated and/or unsaturated carbocycles or by at least 2 carbocycles only one of which is aromatic and forming ortho- or ortho- and peri-condensed systems between them. Generally, the cycles are $C_3$ to $C_8$, preferably $C_6$. More particular examples that can be cited are the bornyl group and the tetrahydronaphthalene group.

$R_a$ and $R_b$ can also independently represent a saturated, unsaturated or aromatic heterocyclic group in particular containing 5 or 6 atoms in the cycle, including one or two heteroatoms such as nitrogen atoms (not substituted with a hydrogen atom), sulphur or oxygen; the carbon atoms of this heterocycle can also be substituted.

$R_a$ and $R_b$ can also represent a polycyclic heterocyclic group defined as either a group constituted by at least two aromatic or non aromatic heterocycles containing at least one heteroatom in each cycle and forming ortho- or ortho- and peri-condensed systems between them, or a group constituted by at least one aromatic or non aromatic hydrocarbon cycle and at least one aromatic or non aromatic heterocycle forming between them ortho- or ortho- and peri-condensed systems; the carbon atoms of said cycles can optionally be substituted.

Examples of heterocyclic type groups $R_a$ and $R_b$ that can be cited include furyl, thienyl, isoxazolyl, furazannyl, isothiazolyl, pyridyl, pyridazinyl, pyrimidinyl, pyrannyl, phosphino and quinolyl, naphthyridinyl, benzopyrannyl or benzofurannyl groups.

The number of substituents present on each cycle depends on the carbon condensation of the cycle and on the presence or otherwise of an unsaturated bond on the cycle. The maximum number of substituents that can be carried by a cycle can readily be determined by the skilled person.

$R_a$ and $R_b$ can be connected to constitute, with the carbon atoms carrying them, a monocyclic or polycyclic, saturated, unsaturated or aromatic carbocyclic or heterocyclic group containing 3 to 20 atoms, comprising two or three ortho-condensed cycles which means that at least two cycles have two carbon atoms in common. In the case of polycyclic compounds, the number of atoms in each cycle is preferably in the range 3 to 6. $R_a$ and $R_b$ preferably form a cyclohexane or fluorenone cycle.

In formulae ($Ia_1$) and ($Ia_2$) for hydrazone type ligands, groups RC preferably represent a hydrogen atom or a $C_1$–$C_4$ alkyl group, an amido group, or an amido group substituted with a $C_1$–$C_4$ alkyl group or with an amino group Preferred hydrazone type ligands have formula ($Ia_1$) or ($Ia_2$) in which $R_c$, which may be identical or different, represent a hydrogen atom or a methyl group and $R_a$ represents one of the following groups:

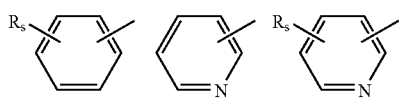

in which $R_s$ represents an alkyl or alkoxy group, preferably $C_1$ to $C_4$, or an amino group which may or may not be substituted with an alkyl group, preferably $C_1$ to $C_4$.

Hydrazone type ligands are produced by reacting:
an aldehyde or ketone with the following formulae:

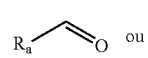 (IIa$_1$)

ou

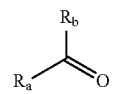 (IIa$_2$)

in which formulae (IIa$_1$) or (IIa$_2$), $R_a$, and $R_b$ have the meanings given in formulae (Ia$_1$) or (Ia$_2$);

with a hydrazine or derivative with formula (IIa$_3$), preferably hydrazine, N-methylhyddrazine or N,N-dimethylhydrazine:

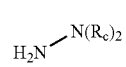 (IIa$_3$)

in which formula (IIa$_3$), $R_c$, which may be identical or different, have the meanings given in formulae (Ia$_1$) or (Ia$_2$).

Preferred hydrazone type ligands used in the process of the invention contain a nitrogen atom supplied by the pyridyl group of a pyridylaldehyde residue. They are preferably obtained by reacting a pyridylaldehyde with a hydrazine or a N-substituted or N,N-disubstituted hydrazine, preferably substituted with an alkyl group containing 1 to 4 carbon atoms.

Examples of preferred ligands are given below:

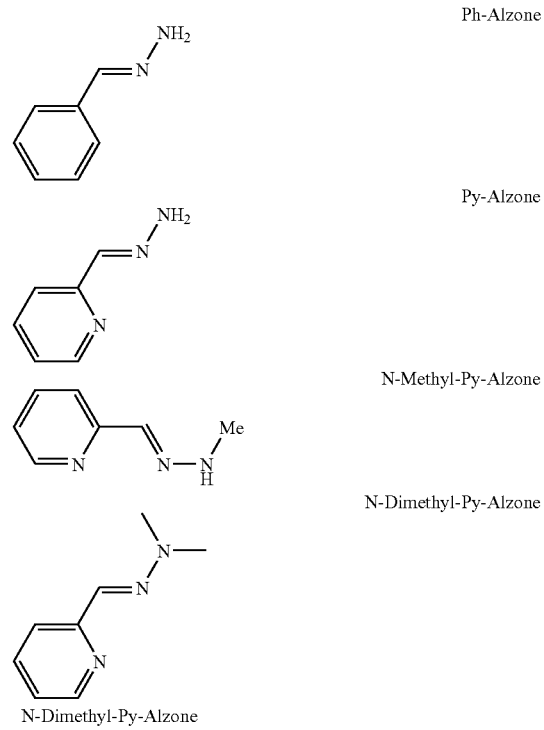

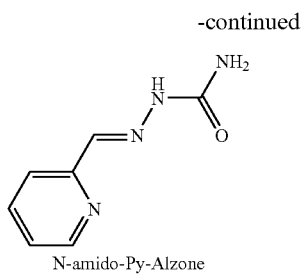

N-amido-Py-Alzone

A further category of ligands that is suitable for carrying out the invention is formed by tetradentate ligands:

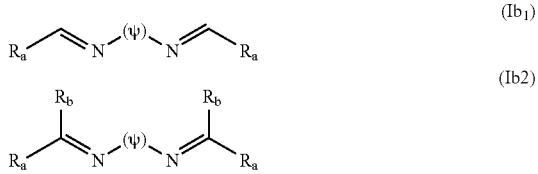

in which formulae:
$R_a$, which may be identical or different, have the meanings given in formulae ($Ia_1$) and ($Ia_2$);
$R_b$, which may be identical or different, have the meanings given in formulae ($Ia_1$) and ($Ia_2$);
Ψ represents a HN—CO—NH— group or a skeleton with general formula ($F_2$) or ($F_3$):

in which formulae ($F_2$) and ($F_3$):
$R_f$ and $R_g$ independently represent a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a concatenation of said groups;
or $R_f$ and $R_g$ can be bonded together to constitute, with the carbon atoms carrying them, a carbocyclic or heterocyclic group containing 3 to 20 atoms, which may be saturated, unsaturated, monocyclic or polycyclic;
$Ar_1$ and $Ar_2$ independently represent two substituted or non substituted aromatic, carbocyclic or heterocyclic cycles which may or may not be condensed, which may carry one or more heteroatoms;
x and y respectively represent the two bonds between the skeleton shown as ψ and the imine groups.

In formulae ($Ib_1$) and ($Ib_2$), symbols $R_a$ and $R_b$ can have the meanings given for formulae ($Ia_1$) and ($Ia_2$).

Preferred tetradentate ligands have formulae ($Ib_1$) or ($Ib_2$) in which $R_b$ represents a hydrogen atom and $R_a$ represents one of the following groups:

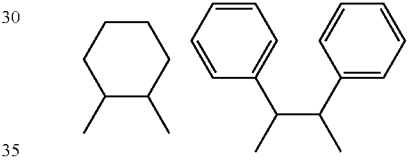

in which $R_s$ represents an alkyl or alkoxy group, preferably $C_1$ to $C_4$, or an amino group which may or may not be substituted with alkyl groups, preferably $C_1$ to $C_4$.

In formulae (F2) and (F3), symbols $R_f$ and $R_g$ can have the meanings given for $R_a$ and $R_b$ in formulae ($Ia_1$) and ($Ia_2$).

Preferably, $R_f$ is identical to $R_g$.

Further, $R_f$ and $R_g$ can also be bonded together to represent saturated, unsaturated or aromatic, monocyclic or polycyclic carbocyclic or heterocyclic groups, preferably bicyclic, which means that at least two cycles have two carbon atoms in common. In the case of polycyclic compounds, the number of carbon atoms in each cycle is preferably in the range 3 to 6.

$R_f$ and $R_g$ can be bonded to constitute, with the carbon atoms carrying them, a saturated or unsaturated, monocyclic or polycyclic, carbocyclic or heterocyclic group containing 3 to 20 atoms, preferably a cyclohexane type cycle.

Illustrative examples of groups ψ that can be mentioned are the following cyclic groups:

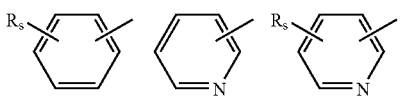

Particularly advantageous compounds have general formula ($F_2$) in which:
$R_f$ and $R_g$ both represent a phenyl or naphthyl group;
$R_f$ and $R_g$ are bonded together to constitute a cycle such as cyclohexane with the carbon atoms carrying them.

In formula ($F_3$), $Ar_1$ and $Ar_2$ together represent an aromatic group which can be a carbocycle containing 6 to 12 carbon atoms or a heterocycle containing 5 to 12 atoms.

In the following description of the present invention, the term "aromatic" designates the conventional idea of aromaticity as defined in the literature, in particular J. March, "Advanced Organic Chemistry", 4th edition, John Wiley & Sons, 1992, pp. 40 ff.

Within the context of the present invention, the aromatic derivative can be monocyclic or polycyclic.

In the case of a monocyclic derivative, it can comprise one or more heteroatoms in its cycle selected from nitrogen, phosphorus, sulphur and oxygen atoms. A preferred mode uses nitrogen atoms not substituted with a hydrogen atom.

Illustrative examples of monocyclic heteroaromatic derivatives that are suitable for use in the present invention that can be cited are pyridine, pyrimidine, pyridazine and pyrazine derivatives.

The carbon atoms of the aromatic derivative can also be substituted. Two neighbouring substituents on the aromatic cycle can also, together with the carbon atoms carrying them, form a hydrocarbon cycle, preferably aromatic, and can if necessary comprise at least one heteroatom. The aromatic derivative is then a polycyclic derivative.

Illustrative examples of this type of compound that can be cited are naphthalene derivatives, quinoline derivatives and isoquinoline derivatives.

Representative examples of compounds with general formula (F₃) that can in particular be cited are those in which Ar₁ and Ar₂ together form either a group deriving from a diphenyl-2,2'-diyl group, or a dinaphthyl-2,2'-diyl group.

The following cyclic groups constitute illustrative examples of groups ψ:

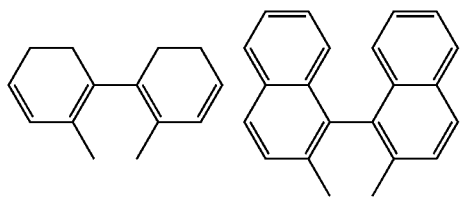

Ligands with formulae (Ib₁) or (Ib₂) are known products. They are obtained by reacting:
an aldehyde or ketone with the following formulae:

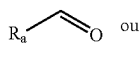
(IIb₁)

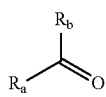
(IIb₂)

in which formulae (IIb₁) or (IIB₂), R$_a$ and R$_b$ have the meanings given in formulae (Ia₁) or (Ia₂);
with a diamine or with formula (IIb₃):

H₂N-ψ-NH₂     (IIb₃)

in which formula (IIb₃), ψ has the meaning given in formulae (Ib₁) or (Ib₂) and represents a group —HN—CO—NH— or a skeleton with general formula (F₂) or (F₃).

Preferred tetradentate type ligands used in the process of the invention contain a nitrogen atom carried by the pyridyl group of a pyridylalkdehyde residue. They preferably result from reacting pyridylaldehyde with urea, 1,2-cyclohexanediamine or 1,2-diphenylethylenediamine.

Examples of preferred ligands are given below:

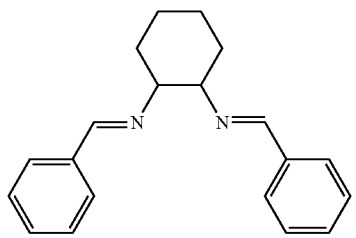

-continued

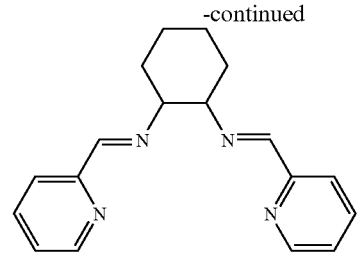

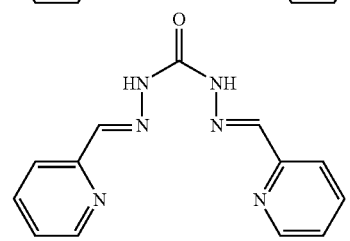

Carbo-Py-Al

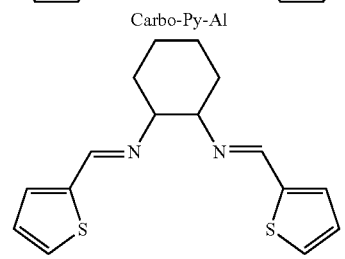

Chxn-Thio-Al

A further category of ligands that can be used in the invention is formed by bidentate ligands with formula:

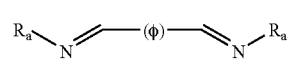
(Ic₁)

in which formula:

R$_a$, which may be identical or different, have the meanings given in formulae (Ia₁) and (Ia₂);

Φ represents:
a covalent bond;
an alkylene group with formula:

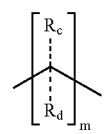

in which R$_c$, R$_d$, which may be identical or different, represent:
a hydrogen atom;
a linear or branched alkyl group containing 1 to 12 carbon atoms, optionally carrying a halogen atom, preferably 1 to 4 carbon atoms, such as methyl, ethyl, propyl, isopropyl, butyl, isobutyl, sec-butyl or tert-butyl;
a halogen atom;
and m equals 0, 1 or 2, preferably 0 or 1;

or the residue of a monocyclic or polycyclic hydrocarbon cycle containing 5 to 12 carbon atoms carrying the two imine functions in the ortho or meta position.

Preferred bidentate type ligands have formula (Ic$_1$) in which groups R$_a$ are identical and represent one of the following groups:

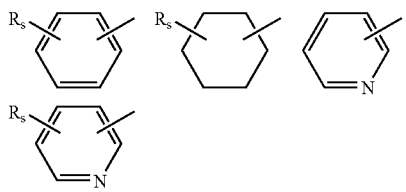

in which R$_s$ represents an alkyl or alkoxy group, preferably C$_1$ to C$_4$.

Preferred bidentate ligands have formula (Ic$_1$) in which 4 represents a covalent bond, a methylene or ethylene group, or a divalent cyclic group such as:

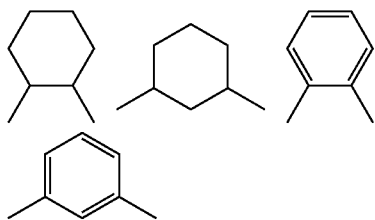

Ligands with formula (Ic$_1$) are produced by reacting:
a dicarbonyl compound with formula:

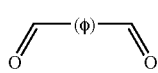

(IIc$_1$)

in which formula (Ic$_1$), ψ has the meanings given in formula (Ic$_1$);
with a primary amine with formula (IIc$_2$)

R$_a$—NH$_2$ (IIc$_2$)

in which formula (IIc$_2$), R$_a$ has the meanings given in formulae (Ia$_1$) or (Ia$_2$).

Preferred ligands with formula (Ic$_2$) used in the process of the invention contain two nitrogen atoms supplied by two imine functions. They preferably result from reacting an α or β carbonylated compound, for example glyoxal, with an amine, preferably cyclohexylamine.

A preferred example of a ligand is given below:

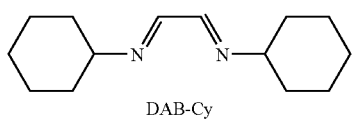

DAB-Cy

Preferred ligands from those cited above are: Chxn-Py-Al, Carbo-Py-Al, Py-Semizone, Chxn-Thio-Al, Py-Alzone and N-Amido-Py-Alzone.

It should be noted that the ligands used in the process of the invention can be employed in an optically pure form or in the form of a racemic mixture.

The different ligands used in the process of the invention are known products.

The quantity in which they are used is a function of the quantity of the metallic element M of the catalyst, preferably copper.

It is generally such that the ratio between the number of moles of ligand and the number of moles of metal is in the range 2 to 1.

It should be noted that the ligand can be introduced concomitantly with the compound supplying the catalytic metallic element. However, the invention also encompasses the case in which a metallic complex is prepared in advance by reacting the compound supplying the catalytic metallic element M and the ligand.

The process of the invention is of importance to a large number of nucleophilic compounds and examples are given below by way of illustration which are not limiting in any way.

A first category of substrates to which the process of the invention is applicable is formed by organic nitrogen-containing derivatives, more particular primary or secondary amines; hydrazine or hydrazone derivatives; amides; sulphonamides; urea derivatives or heterocyclic derivatives, preferably nitrogen-containing and/or sulphur-containing derivatives.

More precisely, the primary or secondary amines can be represented by general formula:

R$_1$R$_2$NH (IIIa)

in which formula (IIIa):
R$_1$, R$_2$, which may be identical or different, represent a hydrogen atom or have the meanings given for R$_a$ and R$_b$ in formula (Ia$_1$) and (Ia2);
at most one of R$_1$ and R$_2$ represents a hydrogen atom.

Preferred amines have formula (IIIa) in which R$_1$, R$_2$, which may be identical or different, represent a C$_1$ to C$_{15}$ alkyl group, preferably C$_1$ to C$_{10}$, a C$_3$ to C$_8$ cycloalkyl group, preferably C$_5$ or C$_6$, or a C$_6$ to C$_{1-2}$ aryl or arylalkyl group.

More particular examples of groups R$_1$ and R$_2$ that can be mentioned are C$_1$ to C$_4$ alkyl groups, phenyl, naphthyl or benzyl groups.

More specific examples of amines with formula (IIIa) that can be mentioned are aniline, N-methylaniline, diphenylamine, benzylamine and dibenzylamine.

It should be noted that the amino group can be in the form of anions. The counter-ion is a metal cation, preferably an alkali metal cation, more preferably sodium or potassium. Examples of such compounds that can be cited are sodium or potassium amide.

Other nucleophilic compounds that can be used in the process of the invention are hydrazine derivatives with formulae (IIb), (IIIc) or (IIId):

NH$_2$—NH—COOR$_3$ (IIIb)

NH$_2$—NH—COR$_4$ (IIIc)

NH$_2$—N=CR$_5$R$_6$ (IIId)

in which formulae (IIb) to (IIId):
R$_3$, R$_4$, R$_5$, R$_6$, which may be identical or different, have the meanings given for R$_1$ and R$_2$ in formula (IIIa).

Groups $R_3$, $R_4$, $R_5$, $R_6$ more particularly represent a $C_1$ to $C_{15}$ alkyl group, preferably $C_1$ to $C_{10}$, a $C_3$ to $C_8$ cycloalkyl group, preferably $C_5$ or $C_6$, or a $C_6$ to $C_{1-2}$ aryl or aryl alkyl group.

In formulae (IIIb) to (IIId), $R_3$ preferably represents a tertiobutyl group, $R_4$ represents a methyl or phenyl group and $R_5$, $R_6$ represent a phenyl group.

The invention also encompasses amide type compounds, more particularly with formula (IIe):

  (IIIe)

In which formula (IIIe), $R_7$ and $R_8$ have the meanings given for $R_1$ and $R_2$ in formula (IIIa).

Examples of compounds with formula (IIIe) that can be cited are oxazolidine-2-one, benzamide and acetamide.

The invention is also applicable to sulphonamide type compounds.

They can have the following formula:

  (IIIf)

In which formula (IIIf), $R_9$ and $R_{10}$ have the meanings given for $R_1$ and $R_2$ in formula (IIIa).

An example of a compound with formula (IIIf) that can be cited is tosylhydrazide.

Other types of nucleophilic substrates that can be mentioned are urea derivatives such as guanidines which can be represented by formula (IIIg):

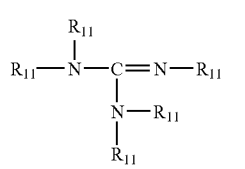  (IIIg)

in which formula (IIIg), groups $R_{11}$, which may be identical or different, have the meanings given for $R_1$ and $R_2$ in formula (IIIa).

An example of a compound with formula (IIIg) that can be cited is N,N,N',N'-tetramethylguanidine.

Nucleophilic substrates that are well suited to use in the process of the invention are heterocyclic derivatives comprising at least one nucleophilic atom such as a nitrogen, sulphur or phosphorus atom.

More precisely, they have general formula (IIIh):

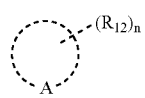  (IIIh)

in which formula (IIIh):
A represents the residue of a cycle forming all or a portion of a monocyclic or polycyclic, aromatic or non aromatic heterocyclic system wherein one of the carbon atoms is replaced by at least one nucleophilic atom such as a nitrogen, sulphur or phosphorus atom;
$R_{12}$, which may be identical or different, represent substituents on the cycle;
n represents the number of substituents on the cycle.

The invention is applicable to monocyclic heterocyclic compounds with formula (IIIh) in which A represents a saturated or non-saturated or aromatic heterocycle in particular containing 5 or 6 atoms in the cycle and possibly containing 1 or 3 heteroatoms such as nitrogen, sulphur or oxygen, at least one of which is a nucleophilic atom such as NH or S.

A can also represent a polycyclic heterocyclic compound defined as being constituted by at least 2 aromatic or non aromatic heterocycles containing at least one heteroatom in each cycle and forming ortho- or ortho- and pericondensed systems between them, or a group constituted by at least one aromatic or non aromatic carbocycle and at least one aromatic or non aromatic heterocycle forming ortho- or ortho- and peri-condensed systems between them.

It is also possible to start from a substrate resulting from a concatenation of a saturated, unsaturated or aromatic heterocycle as described above and a saturated, unsaturated or aromatic carbocycle. The term "carbocycle" preferably means a cycloaliphatic or aromatic cycle containing 3 to 8 carbon atoms, preferably 6.

It should be noted that the carbon atoms of the heterocycle can optionally be substituted with groups $R_{12}$, either completely or partially.

The number of substituents present on the cycle depends on the number of atoms in the cycle and on the presence or otherwise of unsaturated bonds on the cycle.

The maximum number of substituents that can be carried by the cycle can readily be determined by the skilled person.

In formula (IIIh), n is a number equal to 4 or less, preferably 0 or 1.

Examples of substituents are given below, but this list is not limiting in nature.

Group or groups $R_{12}$, which may be identical or different, preferably represent one of the following groups:
- a linear or branched $C_1$ to $C_6$ alkyl group, preferably $C_1$ to $C_4$, such as methyl, ethyl, propyl, isopropyl, butyl, isobutyl, sec-butyl or tert-butyl;
- a linear or branched $C_2$ to $C_6$ alkenyl or alkynyl group, preferably $C_2$ to $C_4$, such as vinyl or allyl;
- a linear or branched $C_1$ to $C_6$ alkoxy or thioether group, preferably $C_1$ to $C_4$ such as methoxy, ethoxy, propoxy, isopropoxy or butoxy, or an alkenyloxy group, preferably an allyloxy or phenoxy group;
- a cyclohexyl, phenyl or benzyl group;
- a group or function such as: hydroxyl, thiol, carboxyl, ester, amide, formyl, acyl, aroyl, amide, urea, isocyanate, thioisocyanate, nitrile, nitride, nitro, sulphone, sulphonic, halogen, pseudohalogen or trifluoromethyl.

The present invention is particularly applicable to compounds with formula (IIIh) in which groups $R_{12}$ more particularly represent an alkyl or alkoxy group.

More particularly, optionally substituted residue A represents one of the following cycles:
- a monocyclic heterocycle containing one or more heteroatoms:

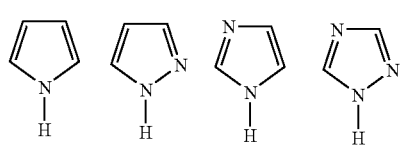

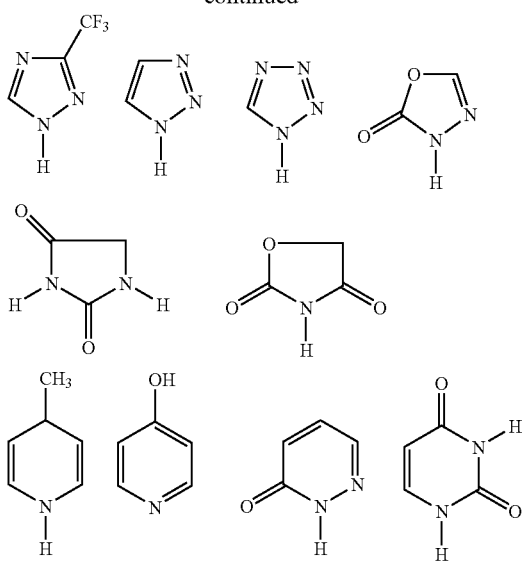

a bicycle comprising a carbocycle and a heterocycle comprising one or more heteroatoms;

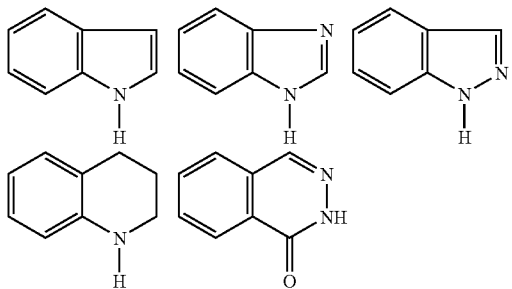

a tricycle comprising at least one carbocycle or a heterocycle comprising one or more heteroatoms;

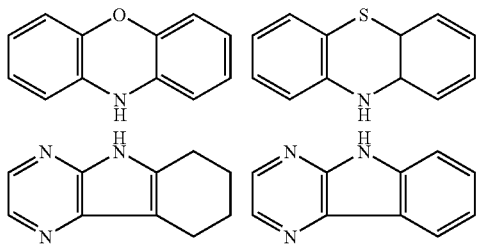

Preferred examples of heterocyclic compounds are those with formula (IIIh) in which A represents a cycle such as: imidazole, pyrazole, triazole, pyrazine, oxadiazole, oxazole, tetrazole, indole, pyrole, phthalazine, pyridazine or oxazolidine.

Nucleophilic compounds that can also be used in the process of the invention that can be cited are alcohol or thiol type compounds represented by the following formula:

$$R_{13}\text{-}Z \qquad \text{(IIIi)}$$

in which formula (IIIi):

$R_{13}$ represents a hydrocarbon group containing 1 to 20 atoms and has the meanings given for $R_1$ or $R_2$ in formula (IIIa);

Z represents a $OM_1$ or $SM_1$ type group in which $M_1$ represents a hydrogen atom or a metallic cation, preferably an alkali metal cation.

Preferred compounds have formula (IIIi) in which $R_{13}$ represents a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a concatenation of said groups.

More precisely, $R_{13}$ preferably represents a linear or branched saturated acyclic aliphatic group preferably containing 1 to 12 carbon atoms, more preferably 1 to 4 carbon atoms.

The invention also encompasses the presence of an unsaturated bond in the hydrocarbon chain such as one or more double bonds, which may or may not be conjugated, or a triple bond.

As mentioned for $R_a$ defined in formula ($Ia_1$) or ($Ia_2$), the hydrocarbon chain can optionally be interrupted by a heteroatom or a functional group, or it may carry one or more substituents.

In formula (IIIi), $R_{13}$ can also represent a saturated or non saturated carbocyclic group, preferably containing 5 or 6 carbon atoms in the cycle; a saturated or non saturated heterocyclic group, containing 5 or 6 carbon atoms in the cycle including 1 or 2 heteroatoms such as nitrogen, sulphur, oxygen or phosphorus atoms; a monocyclic, aromatic heterocyclic carbocyclic group, preferably phenyl, pyridyl, furyl, pyrannyl, thiophenyl, thienyl, phospholyl, pyrazolyl, imidazolyl or pyrolyl, or a polycyclic, aromatic heterocyclic carbocyclic group which may or may not be condensed, preferably naphthyl.

When $R_{13}$ includes a cycle, it can also be substituted. The nature of the substituent is unimportant provided that it does not interfere with the principal reaction. The number of substituents is generally at most 4 per cycle, usually 1 or 2. Reference should be made to the definition of $R_{12}$ in formula (IIIh).

The invention also encompasses the case in which $R_{13}$ comprises a concatenation of aliphatic and/or cyclic, carbocyclic and/or heterocyclic groups.

One acyclic aliphatic group may be connected to a cycle via a covalent bond, a heteroatom or a functional group such as oxy, carbonyl, carboxy, sulphonyl, etc. . . . . .

More particular groups are cycloalkylalkyl, for example cyclohexylalkyl, or aralkyl groups containing 7 to 12 carbon atoms, in particular benzyl or phenylethyl.

The invention also encompasses a concatenation of carbocyclic and/or heterocyclic groups, more particularly a concatenation of phenyl groups separated by a covalent bond or an atom or a functional group G such as: oxygen, sulphur, sulpho, sulphonyl, carbonyl, carbonyloxy, imino, carbonylimino, hydrazo or alkylene ($C_1$–$C_{10}$, preferably $C_1$)-diimino.

The linear or branched, saturated or unsaturated acyclic aliphatic group can optionally carry a cyclic substituent. The term "cycle" means a saturated, unsaturated or aromatic carbocyclic or heterocyclic cycle.

Preferred compounds with formula (IIIi) have general formula (IIIi₁):

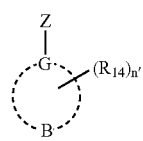

(IIIi₁)

in which:
- B represents the residue of a monocyclic or polycyclic, aromatic, carbocyclic group or a divalent group constituted by a concatenation of two or more monocyclic aromatic carbocyclic groups;
- R₁₄ represents one or more substituents, which may be identical or different;
- Z represents an OM₁ or SM₁ group in which M₁ represents a hydrogen atom or a metallic cation, preferably an alkali metal cation;
- n' is 5 or less.

Examples of substituents R₁₄ can be found by referring to those for R₁₂ defined for formula (IIIh).

More particular compounds with formula (IIIi₁) are those in which residue (B) represents:
- a monocyclic or polycyclic aromatic carbocyclic group with cycles that can together form an ortho-condensed system with formula (F₄):

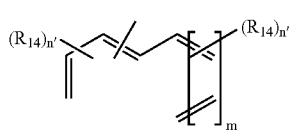

(F₄)

in which formula (F₄), m represents 0, 1 or 2 and symbols R₁₄ and n', which may be identical or different, have the meanings given above;
- a group constituted by a concatenation of two or more monocyclic aromatic carbocyclic groups with formula (F₅):

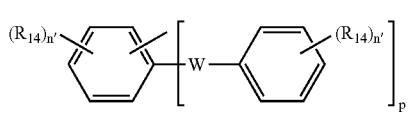

(F₅)

in which formula (F₅), symbols R₁₄ and n', which may be identical or different, have the meanings given above, p is 0, 1, 2 or 3 and w represents a covalent bond, an alkylene or alkylidene C₁ to C₄ group, preferably a methylene group or isopropylidene group, or a functional group such as G.

Preferred compounds with formula (IIIi) have formulae (F₄) and (F₅) in which:
- R₁₄ represents a hydrogen atom, a hydroxyl group, a —CHO group, a —NO₂ group, or a linear or branched alkyl or alkoxy group containing 1 to 6 carbon atoms, preferably 1 to 4 carbon atoms, more preferably methyl, ethyl, methoxy or ethoxy;
- w represents a covalent bond, an alkylene or alkylidene group containing 1 to 4 carbon atoms or an oxygen atom;
- m is 0 or 1;
- n' is 0, 1 or 2;
- p is 0 or 1.

Illustrative examples of compounds with formula (IIIi) that can in particular be mentioned are:
- those in which residue B has formula (F₄) in which m and n' equal 0, such as phenol or thiophenol;
- those in which residue B has formula (F₄) in which n' equals 0 and n equals 1, such as hydroquinone, pyrocatechine, resorcin, alkylphenols, alkylthiophenols, alkoxyphenols, salicylic aldehyde, p-hydroxybenzaldehyde, methyl salicylate, p-hydroxybenzoic acid methyl ester, chlorophenols, nitrophenols or p-acetamidophenol;
- those in which residue B has formula (F₄) in which m equals 0 and n' equals 2, such as dialkylphenols, vanillin, isovanillin, 2-hydroxy-5-acetamidobenzaldehyde, 2-hydroxy-5-propionamidobenzaldehyde, 4-allyloxybenzaldehyde, dichlorophenols, methylhydroquinone or chlorohydroquinone;
- those in which residue B has formula (F₄) in which m equals 0 and n' equals 3, such as 4-bromovanillin, 4-hydroxyvanillin, trialkylphenols, 2,4,6-trinitrophenol, 2,6-dichloro-4-nitrophenol, trichlorophenols, dichlorohydroquinones or 3,5-dimethoxy-4-benzaldehyde;
- those in which residue B has formula (F₄) in which m equals 1 and n' is 1 or more, such as dihydroxynaphthalene, 4-methoxy-1-naphthol or 6-bromo-2-naphthol;
- those in which residue B has formula (F₅) in which p is 1 and n' is 1 or more, such as 2-phenoxyphenol, 3-phenoxyphenol, phenylhydroquinone, 4,4'-dihydroxybiphenyl, isopropylidene 4,4'-diphenol (bisphenol A), bis(4-hydroxyphenyl)methane, bis(4-hydroxyphenyl)sulphone, bis(4-hydroxyphenyl)sulphoxide or tetrabromo bisphenol A.

Other nucleophilic compounds that can be used in the process of the invention are hydrocarbon derivatives containing a nucleophilic carbon.

More particular examples are malonate type anions comprising a —OOC—HC⁻—COO— group.

Alkyl malonate anions with formula (IIIj) can be mentioned:

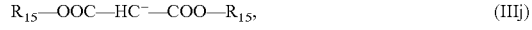

(IIIj)

in which formula (IIIj), R₁₅ and R₁₅', which may be identical or different, represent an alkyl group containing 1 to 12 atoms in the alkyl group, preferably 1 to 4 atoms.

It is also possible to cite malodinitrile type anions containing a NC—HC⁻—CN group.

It is also possible to use nitrile type compounds represented by formula (IIIk):

(IIIk)

in which formula R₁₆ has any nature and has the meanings given for R₁ and also represents a metallic cation, preferably an alkali cation, more preferably lithium, sodium or potassium.

R₁₆ has the meanings given for R₁.

Examples of nitrites that can be mentioned are acetonitrile, cyanobenzene optionally carrying one or more substituents on the benzene ring, or ethanal cyanhydrine CH₃CH(OH)CN.

It is also possible to use acetylenide type compounds in the process of the invention.

They can be represented by the formula (IIIm):

(IIIm)

in which formula R₁₇ is of any nature and the counter-ion is a metal cation, preferably a sodium or potassium atom.

$R_{17}$ has the meanings given for $R_1$.

Particular examples that can be cited are sodium or potassium acetylide or diacetylide.

Other classes of nucleophilic compounds that can be employed in the process of the invention that can be cited are profene type compounds and their derivatives represented by the following formula:

in which formula:

$R_{18}$ has the meanings given for $R_1$;

$R_{19}$ represents an alkyl group containing 1 to 12 atoms in the alkyl group, preferably 1 to 4 atoms.

Preferred compounds are those with formula (IIIn) in which $R_{18}$ represents an alkyl group containing 1 to 12 carbon atoms, a cycloalkyl group containing 5 or 6 carbon atoms and an aryl group containing 6 or 12 carbon atoms or a nitrogen-containing heterocycle containing 5 or 6 atoms.

A further category of nucleophiles that can be used in the process of the invention is formed by amino acids and their derivatives:

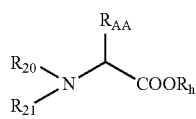

in which formula:

$R_{AA}$ represents the residue of an amino acid, preferably a hydrogen atom, a linear or branched $C_1$ to $C_{12}$ alkyl group optionally carrying a functional group, an aryl group or an arylalkyl $C_6$ to $C_{12}$ group or a functional group, preferably a hydroxyl group;

$R_{20}$ and $R_{21}$ have the meanings given for $R_1$ and $R_2$ in formula (IIIa);

$R_h$ represents a hydrogen atom, a metal cation, preferably an alkali metal cation or a hydrocarbon group containing 1 to 12 carbon atoms, preferably a $C_1$ to $C_{12}$ alkyl group.

In formula (IIIo), $R_{AA}$ represents an alkyl group that can carry a functional group, examples of which that can be cited being an —OH, —NH$_2$, —CO—NH$_2$, —NH—CNH—, —HN—C(O)—NH$_2$—, —COOH, —SH, —S—CH$_3$ group or an imidazole, pyrole or pyrazole group.

Examples of amino acids that can be cited are glycine, cysteine, aspartic acid, glutamic acid and histidine.

Examples of nucleophilic compounds of any other nature that can be mentioned are phosphorus or phosphorus- and nitrogen-containing compounds, more particularly those with the following formulae:

phosphides with formula

phosphines with formula

phosphonium diazoylides with formula

phosphonium azoylides with formula

in which formulae (IIIp) to (IIIs), groups $R_{22}$, which may be identical or different, and group $R_{23}$ represent:

an alkyl group containing 1 to 12 carbon atoms;

a cycloalkyl group containing 5 or 6 carbon atoms;

a cycloalkyl group containing 5 or 6 carbon atoms, substituted with one or more alkyl radicals containing 1 to 4 carbon atoms, or alkoxy radicals containing 1 or 4 carbon atoms;

a phenylalkyl group the aliphatic portion of which contains 1 to 6 carbon atoms;

a phenyl group;

a phenyl group substituted with one or more alkyl radicals containing 1 to 4 carbon atoms or alkoxy containing 1 to 4 carbon atoms or one or more halogen atoms.

More particular examples of phosphorus-containing compounds that can be cited are tricyclohexylphosphine, trimethylphosphine, triethylphosphine, tri-n-butylphosphine, tri-isobutylphosphine, tri-tert-butylphosphine, tribenzylphosphine, dicyclohexylphenylphosphine, triphenylphosphine, dimethylphenylphosphine, diethylphenylphosphine and di-tert-butylphenylphosphine.

Other nucleophilic compounds that can be used include boronic acids or their derivatives, more particularly those with the following formula:

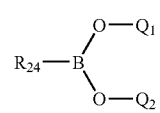

in which:

$R_{24}$ represents a monocyclic or polycyclic, aromatic, carbocyclic or heterocyclic group;

$Q_1$, $Q_2$, which may be identical or different, represent a hydrogen atom, a linear or branched, saturated or unsaturated aliphatic group containing 1 to 20 carbon atoms, or a $R_{24}$ group.

More precisely, the boronic acid has formula (IIIt) in which group $R_{24}$ represents an aromatic carbocyclic or heterocyclic group. $R_{24}$ can have the meanings given above for B in formula (IIIi$_1$). However, $R_{24}$ more particularly represents a carbocyclic group such as a phenyl, naphthyl or heterocyclic group such as a pyrrolyl, pyridyl, pyrimidyl, pyridazinyl, pyrazinyl, 1,3-thiazolyl, 1,3,4-thiadiazolyl or a thienyl group.

The aromatic cycle can also be substituted. The number of substituents is generally at most 4 per cycle, but usually it is 1 or 2. Reference should be made to the definition of $R_{12}$ in formula (IIIh) for examples of substituents.

Preferred substituents are alkyl or alkoxy groups containing 1 to 4 carbon atoms, an amino group, a nitro group, a cyano group, a halogen atom or a trifluoromethyl group.

$Q_1$, $Q_2$, which may be identical or different, more particularly represent a hydrogen atom, or a linear or branched acyclic aliphatic group containing 1 to 20 carbon atoms which may be saturated or contain one or more unsaturated bonds in the chain, preferably 1 to 3 unsaturated bonds, preferably simple or conjugated double bonds.

$Q_1$, $Q_2$, preferably represent an alkyl group containing 1 to 10 carbon atoms, preferably 1 to 4, or an alkenyl group containing 2 to 10 carbon atoms, preferably a vinyl or a 1-methylvinyl group.

$Q_1$, $Q_2$, can have the meanings given for $R_{24}$; in particular, any cycle can also carry a substituent as described above.

Preferably, $R_{24}$ represents a phenyl group.

The scope of the present invention encompasses derivatives of boronic acids such as anhydrides and esters, more particularly alkyl esters containing 1 to 4 carbon atoms.

Particular examples of arylboronic acids that can be cited are: benzeneboronic acid, 2-thiopheneboronic acid; 3-thiopheneboronic acid; 4-methylbenzeneboronic acid, 3-methylthiophene-2-boronic acid, 3-aminobenzeneboronic acid, 3-aminobenzeneboronic acid hemisulphate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid, and esters and anhydrides of said acids.

The present text provides lists of nucleophilic compounds that are in no way limiting and any type of nucleophilic compound can be envisaged.

In accordance with the process of the invention, a —C—C or —C—Nu—(O,S,P,N,Si, B . . . ) bond can be created by reacting a nucleophilic compound with a compound comprising an unsaturated bond in the position α to a leaving group.

More precisely, it is a compound comprising a leaving group Y represented by the formula (IV):

$$R_0—Y \quad (IV)$$

in which formula $R_0$ represents a hydrocarbon group containing 2 to 20 carbon atoms and has a double bond or a triple bond located in the position α to a leaving group Y, or a monocyclic or polycyclic, aromatic, carbocyclic and/or heterocyclic group.

In accordance with the process of the invention, the compound with formula (III) is reacted with a compound with formula (IV) in which:
  $R_0$ represents an aliphatic hydrocarbon group containing a double bond or a triple bond in the position α to the leaving group or a cyclic hydrocarbon group containing an unsaturated bond carrying a leaving group;
  $R_0$ represents a monocyclic or polycyclic, aromatic, carbocyclic and/or heterocyclic group;
  Y represents a leaving group, preferably a halogen atom, or a sulphonic ester group with formula —OSO$_2$—R$_e$, in which $R_e$ is a hydrocarbon group.

The compound with formula (IV) will henceforth be designated as a "compound carrying a leaving group".

In the formula for the sulphonic ester group, $R_e$ is a hydrocarbon group of any nature. However, given that Y is a leaving group, it is advantageous from an economic viewpoint for $R_e$ to be simple in nature, and more particularly to represent a linear or branched alkyl group containing 1 to 4 carbon atoms, preferably a methyl or ethyl group, but it can also represent a phenyl or tolyl group or a trifluoromethyl group, for example. The preferred group Y is a triflate group, which corresponds to a group $R_e$ representing a trifluoromethyl group.

Bromine or chlorine atoms constitute preferred leaving groups.

More particularly, compounds with formula (IV) used in accordance with the process of the invention can be classified into three groups:

(1) aliphatic type compounds, carrying a double bond which can be represented by formula (IVa):

(IVa)

in which formula (IVa):
  $R_{25}$, $R_{26}$ and $R_{27}$, which may be identical or different, represent a hydrogen atom or a hydrocarbon group containing 1 to 20 carbon atoms, which can be a linear or branched, saturated or unsaturated aliphatic group; a monocyclic or polycyclic, saturated, unsaturated or aromatic carbocyclic or heterocyclic group; or a concatenation of aliphatic and/or carbocyclic and/or heterocyclic groups as defined above;
  Y represents the leaving group, as defined above;
(2) aliphatic type compounds, carrying a triple bond, represented by formula (IVb):

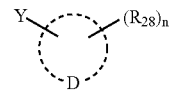

in which formula (IVb):
  $R_{25}$ has the meaning given in formula (IVa);
  Y represents a leaving group as defined above;
(3) aromatic type compounds, hereinafter designated as a "halogenoaromatic compound" and which can be represented by formula (IVc):

$$R_{25}—C≡C—Y \quad (IVb)$$

in which:
  D represents the residue of a cycle forming all or a portion of a monocyclic or polycyclic, aromatic, carbocyclic and/or heterocyclic system;
  $R_{28}$, which may be identical or different, represent substituents on the cycle;
  Y represents a leaving group as defined above;
  n" represents the number of substituents on the cycle.

The invention is applicable to unsaturated compounds with formulae (IVa) and (IVb) in which $R_{25}$ preferably represents a saturated linear or branched acyclic aliphatic group preferably containing 1 to 12 carbon atoms.

The invention does not exclude the presence of a further unsaturated bond on the hydrocarbon chain, such as a further triple bond or one or more double bonds, which may or may not be conjugated.

The hydrocarbon chain can optionally be interrupted by a heteroatom (for example oxygen or sulphur) or by a functional group provided that it does not react; in particular, a group such as —CO— can be cited.

The hydrocarbon chain can optionally carry one or more substituents provided that they do not react under the reaction conditions; particular mention can be made of a halogen atom, a nitrile group or a trifluoromethyl group.

The linear or branched, saturated or unsaturated acyclic aliphatic group can optionally carry a cyclic substituent. The term "cycle" means a saturated, unsaturated or aromatic, carbocyclic or heterocyclic cycle.

The acyclic aliphatic group can be connected to the cycle via a covalent bond, a heteroatom or a functional group such as oxy, carbonyl, carboxy, sulphonyl, etc. . . . .

Examples of cyclic substituents that can be envisaged are cycloaliphatic, aromatic or heterocyclic substituents, in particular cycloaliphatic, containing 6 carbon atoms in the cycle, or benzenic, said cyclic substituents themselves optionally carrying any substituent provided that they do not interfere with the reactions occurring in the process of the invention. Particular mention can be made of alkyl or alkoxy groups containing 1 to 4 carbon atoms.

More particular examples of aliphatic groups carrying a cyclic substituent are aralkyl groups containing 7 to 12 carbon atoms, in particular benzyl or phenylethyl.

In formulae (IVa) and (IVb), $R_{25}$ can also represent a carbocyclic group that may or may not be saturated, preferably containing 5 or 6 carbon atoms in the cycle, preferably cyclohexyl; a heterocyclic group, which may or may not be saturated, in particular containing 5 or 6 carbon atoms in the cycle 1 or 2 of which are heteroatoms such as nitrogen, sulphur or oxygen; a monocyclic aromatic carbocyclic group, preferably phenyl, or a polycyclic aromatic carbocyclic group, which may or may not be condensed, preferably naphthyl.

Regarding $R_{26}$ and $R_{27}$, they preferably represent a hydrogen atom or an alkyl group containing 1 to 12 carbon atoms, or a phenyl group or an aralkyl group containing 7 to 12 carbon atoms, preferably a benzyl group.

In formulae (IVa) and/or (IVb), $R_{25}$, $R_{26}$ and $R_{27}$ more particularly represent a hydrogen atom or $R_{25}$ represents a phenyl group and $R_{26}$, $R_{27}$ represent a hydrogen atom.

Examples of compounds with formulae (IVa) and (IVb) that can be cited are vinyl chloride or bromide, β-bromo- or β-chlorostyrene or bromoalkyne or iodoalkyne.

The invention is of particular application to halogenoaromatic compounds with formula (IVc) in which D is the residue of a cyclic compound, preferably containing at least 4 carbon atoms in its cycle, preferably 5 or 6, optionally substituted, and representing at least one of the following cycles:

a monocyclic or polycyclic aromatic carbocycle, i.e., a compound constituted by at least 2 aromatic carbocycles and between them forming ortho- or ortho- and peri-condensed systems, or a compound constituted by at least 2 carbocycles only one of which is aromatic and between them forming ortho- or ortho- and peri-condensed systems;

a monocyclic aromatic heterocycle containing at least one of heteroatoms P, O, N or S or a polycyclic aromatic heterocycle, i.e., a compound constituted by at least 2 heterocycles containing at least one heteroatom in each cycle wherein at least one of the two cycles is aromatic and between them forming ortho- or ortho- and peri-condensed systems, or a compound constituted by at least one carbocycle and at least one heterocycle at least one of the cycles being aromatic and forming ortho- or ortho- and peri-condensed systems between them.

More particularly, optionally substituted residue D preferably represents the residue of an aromatic carbocycle such as benzene, an aromatic bicycle containing two aromatic carbocycles such as naphthalene; or a partially aromatic bicycle containing two carbocycles one of which is aromatic, such as tetrahydro-1,2,3,4-naphthalene.

The invention also envisages the fact that D can represent the residue of a heterocycle provided that it is more electrophilic than the compound with formula (IIIh).

Particular examples that can be cited are an aromatic heterocycle such as furan or pyridine; an aromatic bicycle comprising an aromatic carbocycle and an aromatic heterocycle such as benzofuran or benzopyridine; a partially aromatic bicycle comprising an aromatic carbocycle and a heterocycle such as methylenedioxybenzene; an aromatic bicycle comprising two aromatic heterocycles such as 1,8-naphthylpyridine; a partially aromatic bicycle comprising a carbocycle and an aromatic heterocycle such as 5,6,7,8-tetrahydroquinoline.

In the process of the invention, a halogenoaromatic compound with formula (IVc) is preferably used in which D represents an aromatic nucleus, preferably a benzene or naphthalene nucleus.

The aromatic compound with formula (IVc) can carry one or more substituents.

In the present text, the term "several" generally means less than 4 substituents $R_{28}$ on the aromatic nucleus.

Reference should be made to the definitions of $R_{12}$ in formula (IIIH) for examples of substituents.

In formula (IVc), n" is a number that is 4 or less, preferably 1 or 2.

Examples of compounds with formula (IVc) that can be cited are p-chlorotoluene, p-bromoanisole and p-bromotrifluorobenzene.

The quantity of compound carrying a leaving group with formula (IV), preferably with formula (IVa) or (IVb) or (IVc), is generally expressed with respect to the quantity of nucleophilic compound and is close to stoichiometry. The ratio between the number of moles of compound carrying a leaving group and the number of moles of nucleophilic compound is usually in the range 0.9 to 1.2.

In accordance with the process of the invention, the nucleophilic compound preferably with formulae (IIIa) to (IIIt) is reacted with a compound carrying a leaving group with formula (IV), preferably with formula (IVa) or (IVb) or (IVc), in the presence of an effective quantity of a catalyst based on a metallic element M selected from group (VIII), (Ib) and (IIb) and a ligand as defined in the invention.

In the present text, reference will be made below to the periodic table published in the Bulletin de la Société Chimique de France, n° 1 (2366).

The different metals M can be used as a mixture, in particular as a mixture with copper.

Examples of metals M that can be cited are copper, silver, palladium, cobalt, nickel, iron and/or zinc.

When a single metal M is used, copper or palladium is preferably selected.

Examples of catalysts that can be used that can be cited are copper metal or organic or inorganic compounds of copper (I) or copper (II).

The catalysts employed in the process of the invention are known products.

Examples of copper catalysts of the invention that can be cited are cuprous bromide, cupric bromide, cuprous iodide, cupric iodide, cupric chloride, basic copper (II) carbonate, cuprous nitrate, cupric nitrate, cuprous sulphate, cupric sulphate, cuprous sulphite, cuprous oxide, cuprous acetate, cupric acetate, cupric trifluoromethylsulphonate, cupric hydroxide, copper (I) methylate, copper (II) methyate and chlorocupric methylate with formula $ClCuOCH_3$.

A palladium catalyst is used in the process of the invention. The palladium can be supplied in the form of a finely divided metal or in the form of an inorganic derivative such as an oxide or hydroxide. It is possible to use a mineral salt, preferably a nitrate, sulphate, oxysulphate, halide, oxyhalide, silicate, carbonate, or an organic derivative, preferably the cyanide, oxalate or acetylacetonate; an alcoholate, more preferably methylate or ethylate; or a carboxylate, still more preferably the acetate. It is also possible to use complexes, in particular chlorine-containing or cyanide containing complexes with palladium and/or alkali metals, preferably sodium, potassium or ammonium.

Examples of compounds that can be used to prepare the catalysts of the invention that can be cited are palladium (II) bromide, palladium (II) chloride, palladium (II) iodide, palladium (II) cyanide, hydrated palladium (II) nitrate, palladium (II) oxide, dihydrated palladium (II) sulphate, palladium (II) acetate, palladium (II) propionate, palladium (II) butyrate, palladium (II) benzoate, palladium (II) acetylacetonate, ammonium tetrachloropalladate (II), potassium hexachloropalladate (IV), palladium (II) tetramine nitrate, palladium (II) dichlorobis(acetonitrile), palladium (II) dichlorobis(benzonitrile), palladium (II) dichloro(1,5-cyclooctadiene), palladium (II) dichlorodiamine, palladium (0) tetrakistriphenylphosphine, palladium (II) acetate and tris-benzylideneacetone palladium (0).

Specific examples of nickel derivatives that can be cited are nickel (II) halides such as nickel (II) chloride, bromide or iodide; nickel (II) sulphate; nickel (II) carbonate; salts of organic acids containing 1 to 18 carbon atoms, in particular the acetate or propionate; nickel (II) complexes such as nickel (II) acetylacetonate, nickel (II) dibromo-bis-(triphenylphosphine), nickel (II) dibromo-bis(pyridine); or nickel (0) complexes such as nickel (0) bis-(cycloocta-1,5-diene) or nickel (0) bis-diphenylphosphinoethane.

It is also possible to use catalysts based on iron or zinc, generally in the form of the oxide, hydroxide or salts such as halides, preferably the chloride, nitrate or sulphate.

Preferably, cupric chloride or bromide and cuprous oxide are selected.

The quantity of catalyst used, expressed as the mole ratio between the number of moles of catalyst and the number of moles of compound with formula (IV), is generally in the range 0.01 to 0.1.

A base, the function of which is to trap the leaving group, is also used in the process of the invention.

The feature of the base is that it has a pKa of 2 or more, preferably in the range 4 to 30.

The pKa is defined as the ionic dissociation constant of the acid/base pair when water is used as the solvent.

Reference should be made, inter alia, to the "Handbook of Chemistry and Physics", 66th edition, p. D-161 and D-162 in order to select a base with a suitable pKa.

Suitable bases that can be cited include mineral bases such as alkali metal carbonates, bicarbonates or hydroxides, preferably of sodium, potassium, caesium or alkaline-earth metals, preferably calcium, barium or magnesium.

It is also possible to use alkali metal hydrides, preferably sodium hydride or alkali metal alcoholates, preferably of sodium or potassium, more preferably sodium methylate, ethylate or tertiobutylate.

It is also possible to use organic bases as tertiary amines, more particularly triethylamine, tri-n-propylamine, tri-n-butylamine, methyldibutylamine, methyldicyclohexylamine, ethyldiisopropylamine, N,N-diethylcyclohexylamine, pyridine, dimethylamino-4-pyridine, N-methylpiperidine, N-ethylpiperidine, N-n-butylpiperidine, 1,2-methylpiperidine, N-methylpyrrolidine and 1,2-dimethylpyrrolidine.

Preferred bases are alkali metal carbonates.

The quantity of base employed is such that the ratio between the number of moles of base and the number of moles of aromatic compound carrying the leaving group is preferably in the range 1 to 4.

The arylation or vinylation or alkynylation reaction of the invention is usually carried out in the presence of an organic solvent.

An organic solvent is used that does not react under the reaction conditions.

The type of solvent used is preferably a polar organic solvent, more preferably aprotic:

linear or cyclic carboxamides such as N,N-dimethylacetamide (DMAC), N,N-diethylacetamide, dimethylformamide (DMF), diethylformamide or 1-methyl-2-pyrrolidinone IMP);

dimethylsulphoxide (DMSO);

hexamethylphosphotriamide (HMPT);

tetramethyurea;

nitro compounds such as nitromethane, nitroethane, 1-nitropropane, 2-nitropropane or mixtures thereof, and nitrobenzene;

aliphatic or aromatic nitrites such as acetonitrile, propionitrile, butanenitrile, isobutanenitrile, pentanenitrile, 2-methylglutaronitrile or adiponitrile;

tetramethylene sulphone (sulpholane);

organic carbonates such as dimethylcarbonate, diusopropylcarbonate or di-n-butylcarbonate;

alkyl esters such as ethyl or isopropyl acetate;

halogenated or non halogenated aromatic hydrocarbons such as chlorobenzene or toluene;

ketones, such as acetone, methylethylketone, methylisobutylketone, cyclopentanone, cyclohexanone;

nitrogen-containing heterocycles such as pyridine, picoline and quinolines.

It is also possible to use a mixture of solvents.

The quantity of organic solvent to be used is determined as a function of the nature of the selected organic solvent.

It is determined so that the concentration of the compound carrying a leaving group in the organic solvent is preferably in the range 5% to 40% by weight.

The arylation or vinylation or alkynylation reaction of the nucleophilic compound takes place at a temperature that is advantageously in the range 0° C. to 120° C., preferably in the range 20° C. to 100° C., more preferably in the range 25° C. to 85° C.

The arylation or vinylation or alkynylation reaction is generally carried out at atmospheric pressure, but higher pressures of up to 10 bars, for example, can also be used.

In practice, the reaction is simple to carry out.

The order of using the reagents is not critical. Preferably, the (preferably copper) catalyst, the ligand, the nucleophilic compound with formula (III), the base, the compound carrying a leaving group with formula (IV) and the organic solvent are charged.

The reaction medium is heated to the desired temperature.

The progress of the reaction is monitored by following the disappearance of the compound carrying a leaving group.

At the end of the reaction, a product of the type R—Nu—R₀ is obtained, more particularly an arylated compound comprising the residue of the nucleophilic compound and the residue of an electrophilic compound preferably with the following formula (V):

in which formula (V), D, R, $R_{29}$, Nu and n″ have the meanings given above.

The compound obtained is recovered using conventional techniques, in particular by crystallisation from an organic solvent.

More specific examples of organic solvents that can be mentioned are aliphatic or aromatic, halogenated or non halogenated hydrocarbons, carboxamides and nitriles. Particular mention can be made of cyclohexane, toluene, dimethylformamide and acetonitrile.

Examples of the invention will now be given. These examples are given by way of illustration and are not limiting in nature.

Before describing the examples, we shall describe the operating protocol used in all of the examples unless otherwise indicated. The preparation of certain ligands and catalysts is also illustrated.

In the examples, the degree of transformation (TT) corresponds to the ratio between the number of moles of substrate transformed and the number of moles of substrate engaged.

The yield (RR) corresponds to the ratio between the number of moles of product formed and the number of moles of substrate engaged.

The transformation yield (RT) or selectivity corresponds to the ratio between the number of moles of product formed and the number of moles of substrate engaged.

EXAMPLES

Operating Protocol

The following are successively introduced into a 35 ml Schlenk tube placed in a nitrogen atmosphere:
copper catalyst (0.05 mmoles);
ligand (0.1 mmoles);
nucleophilic compound (0.75 mmoles);
a base (1 mmoles);
56 µl of iodobenzene (0.5 mmoles);
and 300 µl of acetonitrile.

The mixture is placed in an oil bath at a temperature of 50° C. and stirred for 90 hours.

After this period, the mixture is diluted with ethyl ether or dichloromethane.

65 µl of internal reference (1,3-dimethoxybenzene) is introduced and a sample of reaction medium is removed then filtered over celite (or filter medium) eluting with ethyl ether or dichloromethane depending on the solubility.

The arylated compound obtained is extracted with ethyl ether or dichloromethane, then with distilled water and the product obtained is analysed by gas chromatography using 1,3-dimethoxybenzene as an internal reference.

Preparation of Ligands:

a Preparation of trans-1,2-bis(2'-pyridylidenamino)-cyclohexane (Chxn-Py-Al) with formula:

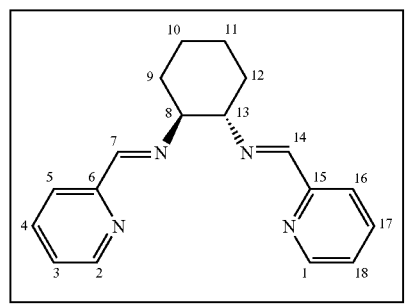

The ligand was prepared using the method described by Gao. H-X; Zhang, H.; Yi, X-D; Xu, P.-P.; Tang, C.-L.; Wan, H.-L.; Tsai, K.-R.; Ikariya, T.; (Chirality 2000, 12, 383–388).

12.65 g of anhydrous magnesium sulphate (105.1 mmoles) and 4.2 ml of a racemic trans-1,2-diaminocyclohexane mixture (35.0 mmoles) were successively added to a solution of 6.66 ml of 2-pyridylaldehyde (70.0 mmoles) in 50 ml of absolute ethanol.

The reaction mixture was stirred for 20 hours at ambient temperature (the solution turned yellow after stirring for three hours), heated for 2.5 hours under reflux, then filtered through a frit.

The isolated solid was washed with dichloromethane.

The total filtrate was concentrated completely under reduced pressure to isolate an ochre solid, which was re-crystallised from ethanol.

8.2 g of pale yellow crystals were obtained, which corresponded to a 80.1% yield.

The characteristics were as follows:

M.Pt: 140–141° C. (EtOH) (racemic mixture) (Lit: 127–129° C.: obtained by Belokon, Y N; North, M: Churkina, T D; Ikonnikov, N S; Maleev, V I; Tetrahedron 2001, 57, 2491–2498 for the stereoisomer 1S,2S, hexane-MeOH);

$^1$H NMR/CDCl$_3$: δ 8.51 (m, 2H, H$_{1,2}$), 8.28 (s, 2H, H$_{7,14}$), 7.84 (m, 2H, H$_{4,17}$), 6.55–7.64 (m, 2H, H$_{5,16}$), 7.14–7.21 (m, 2H, H$_{3,18}$), 3.50 (m, 2H, H$_{8,13}$), 1,81 (m, 6H, H$_{10,11}$ and H carried by carbons 9 and 12 located in the position cis (or trans) with respect to the adjacent nitrogen atoms), 1.40–1.53 (m, 2H, H carried by carbons 9 and 12 located in the trans (or cis) position with respect to the adjacent nitrogen atoms).

$^{13}$C NMR/CDCl$_3$: δ 161.42 (C7 and C14), 154.61 (C6 to C15), 149.21 (C1 and C2), 136.39 (C4 and C17), 124.43 (C3 and C18), 121.29 (C5 and C16), 73.53 (C8 and C13), 32.70 (C9 and C12), 24.33 (C10 and C11).

FAB+ (NBA matrix): 293 (100%, M+1), 107 (52%, 2-pyridylaldimine+H$^+$), 92 (38%, C$_5$H$_4$N—CH$_2$$^+$), 119 (25%, C$_5$H$_4$N—CH=N—CH$_2$$^+$), 294 (23%, M+2), 204 (22%, [M-(2-pyridylidene)]$^+$), 79 (21%, pyridine$^+$), 187 (20%, M-[2-pyridylineamino]$^+$), 585 (1%, 2M+1).

b. Preparation of bis-(2-pyridylidene)-carbohydrazide (Carbo-Py-Al) with formula:

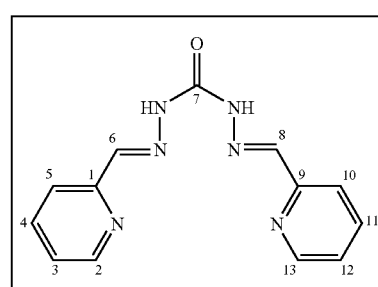

The ligand was prepared using the method described by Exner O; Kliegman, J M; J. Org. Chem. 1971, 36, 2014–2015.

8.96 g of anhydrous sodium sulphate (63.1 mmoles) and 4.0 ml of 2-pyridylaldehyde (42.05 mmoles) were added in succession to a suspension of 1.89 g of carbohydrazide (21.0 mmoles) in 150 ml of absolute ethanol.

The reaction mixture was heated for 4 hours under reflux then filtered through a frit (the disappearance of the 2-pyridylaldehyde was monitored by gas chromatography).

The retained solid was washed with copious amounts of absolute ethanol to dissolve the product obtained.

The filtrate was concentrated to isolate a colourless solid, which was oven dried at 100° C. then re-crystallised from methanol.

4.53 g of colourless crystals were obtained, corresponding to a yield of 80.5%.

The characteristics were as follows:

M.Pt: 219–220° C.;

$^1$H NMR/DMSO-$d_6$: δ 11.08 (wide s, 2H, NH), 8.58 (m, 2H, $H_{2,13}$), 8.25 (wide s, 2H, $H_{6,8}$), 8.12 (m, 2H, $H_{5,10}$), 7.87 (m, 2H, $H_{4,11}$), 7.38 (m, 2H, $H_{3,12}$);

$^{13}$C NMR/DMSO-$d_6$: δ 153.46 (C7), 151.64 (C1 and C19), 149.26 (C2 and C13), 143.69 (C6 and C8), 136.52 (C4 and C11), 123.83 (C3 and C12), 119.75 (C5 and C10);

FAB+ (NBA matrix): 269 (60%, M+1), 148 (51%, [$C_5H_4NCH=N-NHCO$]$^+$), 122 (44%, $C_5H_4N-CH=N-NH_3^+$), 107 (41%, 2-pyridylaldimine+H$^+$), 537 (4%, 2M+1), 559 (1%, 2M+Na$^+$).

c. Preparation of 2-pyridylaldehyde N-methylhydrazone (Py-Alzone) with formula:

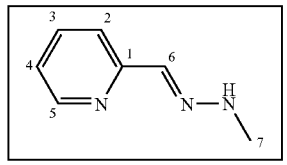

The ligand was prepared using the method described by Exner O; Kliegman, J M; J. Org. Chem. 1971, 36, 2014–2015.

8.96 g of anhydrous sodium sulphate (63.07 mmoles) and 2.24 ml of N-methylhydrazine (42.05 mmoles) were added in succession to a solution of 2.0 g of 2-pyridylaldehyde (21.02 mmoles) in 50 ml of absolute ethanol.

The reaction mixture was heated for 30 minutes at ambient temperature, then heated for 20 hours under refulx, then filtered through a frit.

The isolated sodium sulphate was washed with diethyl ether.

The total filtrate was concentrated completely under reduced pressure.

The orange oil obtained underwent the usual treatment (extraction with diethyl ether/water).

After drying over magnesium sulphate, filtering and concentration under reduced pressure, the yellow oil obtained was re-crystallised from methanol.

The crystals obtained were washed with copious quantities of petroleum ether to render them colourless.

1.4 g of crystals were obtained, corresponding to a yield of 49%.

The compound was relatively unstable and had to be prepared just prior to use.

The characteristics were as follows:

M.Pt: 44–45° C. (Lit: 39–40° C., obtained by Renwick, G M; Aust. J. Chem. 1970, 23, 2109–2117);

$^1$H NMR/CDCl$_3$: δ 8.50 (m, 1H, H$_5$), 7.71–7.76 (m, 1H, H$_2$), 7.57–7.66 (m, 1H, H$_3$), 7.55 (s, 1H, H$_6$), 7.07–7.14 (m, 1H, H$_4$), 5.92 (wide s, 1H, NH), 3.00 (s, 3H, H$_7$);

$^{13}$C NMR/CDCl$_3$: δ 155.44 (C1), 149.09 (C5), 136.21 (C3), 134.10 (C6), 121.92 (C4), 119.04 (C2), 34.07 (C7);

GC/MS: Rt=13.75 min, M/Z=135, purity=100%.

d Preparation of 2-pyridylaldehyde semicarbazone (N-amido-PY-Alzone) with formula:

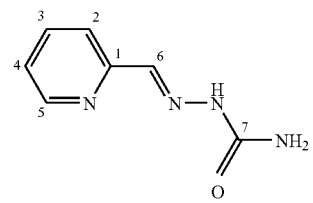

7.35 ml of triethylamine (52 mmoles) was added to a suspension of 5.8 g of semicarbazide hydrochloride (52 mmoles) in 60 ml of absolute ethanol.

The solution was heated to 50° C. then 5 ml of 2-pyridylaldehyde was rapidly added.

The mixture was heated under reflux for two hours, cooled to 20° C. then filtered through a frit.

The isolated yellow solid was washed with copious amounts of water, oven dried at 100° C. then re-crystallised from ethanol.

2.6 g of colourless crystals were otbained, which corresponded to a yield of 30%.

M.Pt: 204–206° C. (Lit: 206° C., EtOH obtained by Case, F H; Schilt, A A, J. Chem. Eng. Data 1980, 25, 404–405);

$^1$H NMR/DMSO-$d_6$: δ 10.56 (wide s, 1H, NH), 8.51 (m, 1H, H$_5$), 8.13 (m, 1H, H$_2$), 7.90 (s, 1H, H$_6$), 7.77 (m, 1H, H$_3$), 7.30 (m, 1H, H$_4$), 6.68 (wide s, 2H, NH$_2$);

$^{13}$C NMR/DMSO-$d_6$: δ 156.57 (C7), 153.66 (C1), 149.03 (C5), 139.85 (C3), 136.32 (C6), 123.39 (C4), 119.50 (C2).

e—Preparation of trans-1,2-bis(2'-thienylideneamino)-cyclohexane (Chxn-Tho-Al) with formula:

This ligand has been described by Van Stein, G C; Van Loten, G; Vrieze, K, Inorg. Chem 1985, 24 (9), 1367–1375.

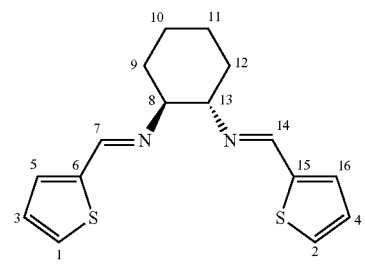

19.36 g of anhydrous magnesium sulphate (161.1 mmoles) and 6.44 ml of rac-trans-1,2-diaminocyclohexane (53.6 mmoles) were successively added to a solution of 10 ml of 2-thienylaldehyde (107.1 mmoles) in 75 ml of absolute ethanol.

The reaction mixture was stirred for 16 hours at ambient temperature (the solution thickened very rapidly), heated for 2 hours under reflux then filtered through a frit.

The isolated solid was washed with dichloromethane.

The total filtrate was concentrated completely under reduced pressure to isolate a brown solid which was re-crystallised from ethanol.

14.0 g of beige crystals were obtained, corresponding to a yield of 86%.

The characteristics were as follows:

M.Pt: 173–175° C. (EtOH);

$^1$H NMR/CDCl$_3$: δ 8.27 (s, 2H, H$_{7,14}$), 7.27 (m, 2H, H,$_2$), 7.14 (m, 2H, H$_{5,16}$), 6.96 (m, 2H, H$_{3,4}$), 3.32 (m, 2H, H$_{8,13}$), 1.82 (m, 6H, H$_{10,11}$ and H carried by carbons 9 and 12 located in the position cis (or trans) with respect to the adjacent nitrogen atoms), 1.44 (m, 2H, H carried by carbons 9 and 12 located in the trans (or cis) position with respect to the adjacent nitrogen atoms).

$^{13}$C NMR/CDCl$_3$: δ 154.32 (C7 and C14), 142.54 (C6 to C15), 130.09 (C1 and C2), 128.20 (C5 and C16), 127.18 (C3 and C4), 73.38 (C8 and C13), 32.83 (C9 and C12), 24.44 (C10 and C11).

f—Preparation of Glyoxal Dicyclohexylimine (DAB-Cy) with Formula:

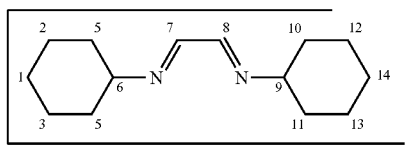

A mixture composed of 6.53 g of an aqueous solution of 40% by weight glyoxal (45.0 mmoles of glyoxal), 7 ml of n-propanol and 20 ml of water was added to a solution of 10 g of cyclohexylamine (100.8 mmoles) in 70 ml of n-propanol.

After heating for one and a half hours at 70° C., the mixture was cooled to ambient temperature.

Adding 100 ml of ice water caused precipitation of a large amount of white solid.

It was isolated by filtering through a frit, washed with water (3×50 ml) and methanol (1×25 ml) then vacuum dried.

8.5 g of product was obtained, corresponding to a yield of 86%.

The characteristics were as follows:

M.Pt: 144–145° C. (Literature: 145–147° C., obtained by Exner O; Kliegman, J M; J. Org. Chem. 1971, 36, 2014–2015);

$^1$H NMR/CDCl$_3$: δ 7.92 (s, 2H, H$_{7,8}$), 3.14 (m, 2H, H$_{6,9}$), 1.17–1.82 (m, 20H, H$_{1,2,3,4,5,10,11,12,13,14}$);

$^{13}$C NMR/CDCl$_3$: δ 160.10 (C7 and C8), 69.39 (C6 to C9), 33.95 (C4, C5, C10 and C11), 25.50 (C1 and C14), 24.57 (C2, C3, C12 and C13).

Preparation of Catalysts:

The catalysts used were commercially available products with the exception of activated Cu (A) and activated Cu (B). An operating mode is also provided for preparing said catalysts, which were then used in the examples.

a—Activated Cu (A) Prepared by Purification of Metallic Copper:

A few grams of copper powder were ground for 15 minutes in a solution composed of 2 g of iodine dissolved in 100 ml of acetone.

The mixture was filtered through a frit, washed with 150 ml of a solution composed of concentrated hydrochloric acid (75 ml) and acetone (75 ml), using 100 ml of acetonitrile then 100 ml of acetone.

Elimination of all of the cuprous iodide was ensured by washing with acetonitrile, a solvent in which it is highly soluble (27.51 g/l).

The activated copper was dried in a vacuum dessiccator in the presence of P$_2$O$_5$.

It was used immediately after its preparation.

b—Activated Cu (B) Prepared by Reduction of Copper Sulphate:

30 g of copper sulphate pentahydrate (120 mmoles) was dissolved in a solution composed of 100 ml of distilled water and 5 ml of hydrochloric acid.

1.96 g of zinc (30 mmoles) was slowly added to this solution, taking care that the temperature did not exceed 40° C.

The precipitated copper was isolated by filtering through a frit, washed with distilled water then with acetone and dried in a desiccator in the presence of P$_2$O$_5$.

It was used after preparation.

Example 1

N-arylation and N-vinylation of Azoles

Several operating protocols will now be given; their choice depends on the physical form of the nucleophile and the arylation agent.

Operating Protocol A: Solid Nucleophile and Liquid Arylation Agent 14.4 mg of cuprous oxide (0.1 mmoles), 116.8 mg of Chxn-Py-Al or another ligand as generally defined in this patent (0.4 mmoles), 3 mmoles of a nucleophilic compound and 1.303 g of caesium carbonate (4 mmoles) are successively introduced into a 35 ml Schlenk tube that has been oven dried at 100° C. and is provided with a magnetic stirrer (12×4.5 mm) and under a nitrogen atmosphere.

The Schlenk tube is purged under vacuum then refilled with nitrogen.

2 mmoles of arylation agent then 1.2 ml of acetonitrile or DMF are then added using syringes.

The reactor is placed in an oil bath at a temperature of 82° C. and stirred for a period of one to five days.

Operating Protocol B: Solid Nucleophile and Solid Arylation Agent 14.4 mg of cuprous oxide (0.11 mmoles), 116.8 mg of Chxn-Py-Al or another ligand as generally defined in this patent (0.4 mmoles), 3 mmoles of a nucleophilic compound, 2 mmoles of arylation agent and 1.303 g of caesium carbonate (4 mmoles) are successively introduced into a 35 ml Schlenk tube that has been oven dried at 100° C. and is provided with a magnetic stirrer (12×4.5 mm) and under a nitrogen atmosphere.

The Schlenk tube is purged under vacuum then refilled with nitrogen.

1.2 ml of acetonitrile or DMF is then added using a syringe.

The reactor is placed in an oil bath at a temperature of 82° C. and stirred for a period of one to five days.

Operating Protocol C: Liquid Nucleophile and Arylation Agent 14.4 mg of cuprous oxide (0.1 mmoles), 116.8 mg of Chxn-Py-Al or another ligand as generally defined in this patent (0.4 mmoles) and 1.303 g of caesium carbonate (4 mmoles) are successively introduced into a 35 ml Schlenk tube that has been oven dried at 100° C. and is provided with a magnetic stirrer (12×4.5 mm) and under a nitrogen atmosphere.

The Schlenk tube is purged under vacuum then refilled with nitrogen.

3 mmoles of a nucleophilic compound, 2 mmoles of arylation agent and 1.2 ml of acetonitrile or DMF are then added using syringes.

The reactor is placed in an oil bath at a temperature of 82° C. and stirred for a period of one to five days.

Operating Protocol D: Liquid Nucleophile and Solid Arylation Agent 14.4 mg of cuprous oxide (0.1 mmoles), 116.8 mg of Chxn-Py-Al or another ligand as generally defined in this patent (0.4 mmoles), 2 mmoles of a arylation agent and 1.303 g of caesium carbonate (4 mmoles) are successively introduced into a 35 ml Schlenk tube that has been oven dried at 100° C. and is provided with a magnetic stirrer (12×4.5 mm) and under a nitrogen atmosphere.

The Schlenk tube is purged under vacuum then refilled with nitrogen.

3 mmoles of nucleophilic compound and 1.2 ml of acetonitrile or DMF are then added using syringes.

The reactor is placed in an oil bath at a temperature of 82° C. and stirred for a period of one to five days.

Whichever operating protocol, A, B, C or D is used, the rest of the treatment is rigorously identical.

Determination of Isolated Yield:

After the period, the reaction mixture is diluted with 25 ml of dichloromethane, filtered through celite, concentrated completely under reduced pressure (about 20 mm of mercury) then taken up in 50 ml of dichloromethane.

This organic phase is extracted with distilled water (2×20 ml).

The aqueous phase is extracted again with 20 ml of dichloromethane.

The total organic phase is washed with a saturated aqueous sodium chloride solution (2×20 ml), dried over MgSO$_4$, filtered and concentrated under reduced pressure.

The residue obtained is purified by silica gel chromatography (35–70 µm).

Determination of Degree of Transformation:

After the period, 65 µl of 1,3-dimethoxybenzene (internal reference) is introduced into the cooled reaction medium, which is then diluted with 5 ml of diethyl ether or dichloromethane, depending on the solubility of the products to be analysed.

An aliquot is then removed, filtered through celite (or filter medium composed of about 90% SiO$_2$), eluting with diethyl ether or dichloromethane, extracted three times with distilled water then analysed by gas chromatography.

Example 1.1

Preparation of 1-phenyl-1H-pyrazole

Operating protocol A (82° C., 24 hours) was followed using 120.8 mg of Chxn-Thio-Al (0.4 mmoles), 211 µl of bromobenzene (2 mmoles), 204 mg of pyrazole (3 mmoles) and 1.2 ml of acetonitrile.

The residue obtained was purified by silica gel chromatography (eluent: dichloromethane/petroleum ether 60/40).

A colourless liquid was obtained in a yield of 80% by weight.

The compound obtained had the following formula:

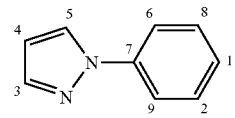

The characteristics were as follows:

B.Pt: 58° C., 0.2 mm Hg (Lit: 58–60° C., 0.2 mm Hg);

$^1$H NMR/CDCl$_3$ (250 MHz): δ 7.92 (dd, 1H, $^3J_{HH}$=2.4 Hz, $^4J_{HH}$=0.5 Hz, H$_5$), 7.70 (m, 3H, H$_{3,6,9}$), 7.45 (m, 2H, H$_{2,8}$), 7.29 (s, 1H, H$_1$), 6.46 (dd, 1H, $^3J_{HH}$=2.4 Hz, $^3J_{HH}$=1.8 Hz, H$_4$);

$^{13}$C NMR/CDCl$_3$: δ 141.08 (C3), 140.23 (C7), 129.43 (C2 and C8), 126.75 (C5), 126.44 (C1), 119.21 (C6 and C9), 107.61 (C4);

GC/MS: Rt=15.37 min, M/Z=144, purity=100%;

Rf=0.40 (eluent: dichloromethane/petroleum ether, 60/40).

Example 1.2

Preparation of 1-phenyl-1H-pyrazole

Operating protocol A (82° C., 24 hours) was followed using 117 mg of Chxn-Py-Al (0.4 mmoles), 211 µl of bromobenzene (2 mmoles), 204 mg of pyrazole (3 mmoles) and 1.2 ml of acetonitrile.

The residue obtained was purified by silica gel chromatography (eluent: dichloromethane/petroleum ether 60/40).

A yield of 93:1% by weight of 1-phenyl-1H-pyrazole was obtained with formula:

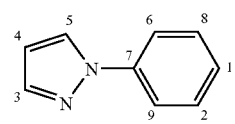

Example 1.3

Preparation of 1-phenyl-1H-pyrazole

Operating protocol A (82° C., 24 hours) was followed using 54 mg of Py-Alzone (0.4 mmoles), 211 µl of bromobenzene (2 mmoles), 204 mg of pyrazole (3 mmoles) and 1.2 ml of acetonitrile.

The residue obtained was purified by silica gel chromatography (eluent: dichloromethane/petroleum ether, 60/40).

A yield of 96.7% by weight of 1-phenyl-1H-pyrazole was obtained with formula:

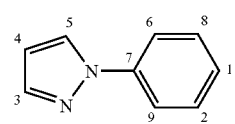

Example 1.4

Preparation of 1-phenyl-1H-pyrazole

Operating protocol A (82° C., 24 hours) was followed using 65.6 mg of N-Amido-Py-Alzone (0.4 mmoles), 211 µl of bromobenzene (2 mmoles), 204 mg of pyrazole (3 mmoles) and 1.2 ml of acetonitrile.

The residue obtained was purified by silica gel chromatography (eluent: dichloromethane/petroleum ether 60/40).

A yield of 95.2% by weight of 1-phenyl-1H-pyrazole was obtained with formula:

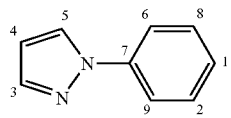

Example 1.5

Preparation of 1-phenyl-1H-pyrazole

Operating protocol A (82° C., 24 hours) was followed using 107.2 mg of Carbo-Py-Al (0.4 mmoles), 211 µl of bromobenzene (2 mmoles), 204 mg of pyrazole (3 mmoles) and 1.2 ml of acetonitrile.

The residue obtained was purified by silica gel chromatography (eluent: dichloromethane/petroleum ether 60/40).

A yield of 75% by weight of 1-phenyl-1H-pyrazole was obtained with formula:

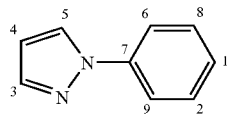

Example 1.6

Preparation of 1-(o-tolyl)-1H-pyrazole

Operating protocol A (82° C., 70 hours) was followed using 117 mg of Chxn-Py-Al (0.4 mmoles), 383 µl of 2-iodotoluene (3 mmoles), 136 mg of pyrazole (2 mmoles) and 1.2 ml of acetonitrile.

The degree of transformation and selectivity for 1-(o-tolyl)-1H-pyrazole were 100%.

The residue obtained was purified by silica gel chromatography (eluent: hexane/dichloromethane, 100/0 to 0/100).

297 mg of a pale yellow oil was obtained, corresponding to a yield of 94% by weight.

The compound obtained had the following formula:

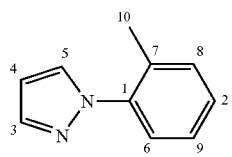

Example 1.7

Preparation of 1-(4'-bromophenyl)-1H-pyrazole

Operating protocol B (82° C., 72 hours) was followed using 117 mg of Chxn-Py-Al (0.4 mmoles), 1.887 g of 1,4-dibromobenzene (8 mmoles), 136 mg of pyrazole (3 mmoles) and 1.6 ml of acetonitrile.

The degree of transformation and selectivity for 1-(4'-bromophenyl)-1H-pyrazole were 89%.

The residue obtained was purified by silica gel chromatography (eluent: hexane/dichloromethane, 100/0 to 50/50).

366 mg of a colourless solid was obtained, corresponding to a yield of 82% by weight.

The compound obtained had the following formula:

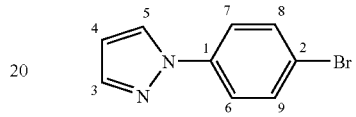

The characteristics were as follows:

M Pt: 71° C. (MeOH) (Lit: 70° C., aqueous MeOH obtained by Khan, M A; Lynch, B M; Hung, Y-Y; Can. J. Chem. 1963, 41,1540–1547);

$^1$H NMR/CDCl$_3$ (250 MHz): δ 7.88 (dd, 1H, $^3J_{HH}$=2.5 Hz, $^4J_{HH}$=0.5 Hz, H$_5$), 7.72 (dd, 1H, $^3J_{HH}$=1.7 Hz, $^4J_{HH}$=0.5 Hz, H$_3$), 7.52–7.62 (m, 4H, H$_{6,7,8,9}$), 6.46 (dd, 1H, $^3J_{HH}$=1.7 Hz, $^3J_{HH}$=2.5 Hz, H$_4$);

$^{13}$C NMR/CDCl$_3$: δ 141.41 (C3), 139.21 (C1), 132.46 (C6 and C7), 126.64 (C5), 120.59 (C8 and C9), 119.62 (C2), 108.83 (C4);

GC/MS: Rt=16.90 min, M/Z=222 and 224, purity=100%; Rf=0.21 (eluent: hexane/dichloromethane, 50/50).

Example 1.8

Preparation of 1-(4-imidazol-1-yl-phenyl)-1H-pyrazole

Operating protocol B (82° C., 48 hours) was followed using 117 mg of Chxn-Py-Al (0.4 mmoles), 535 mg of 1-(4'-bromophenyl)-1H-imidazole (2.4 mmoles), 136 mg of pyrazole (2 mmoles) and 1.2 ml of acetonitrile.

The residue obtained was purified by silica gel chromatography (eluent: dichloromethane/methanol, 100/0 to 98/2).

387 mg of a colourless solid was obtained, corresponding to a yield of 92% by weight.

The compound obtained had the following formula:

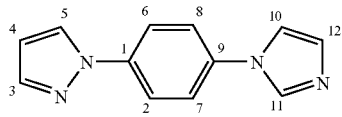

The characteristics were as follows:

M Pt: 174–176° C.;

$^1$H NMR/acetone-d$_6$ (250 MHz): δ 8.40 (dd, 1H, $^3J_{HH}$=2.5 Hz, $^4J_{HH}$=0.6 Hz, H$_5$) 8.15 (wide s, 1H, H$_{11}$), 7.98–8.04 (m, 2H, H$_{7,8}$), 7.73–7.79 (m, 2H, H$_{2,6}$), 7.73 (dd, 1H, $^3J_{HH}$=1.7 Hz, $^4J_{HH}$=0.6 Hz, H$_3$), 7.66 (wide s, 1H, H$_{10}$), 7.16 (wide s, 1H, H$_{12}$), 6.54 (dd, 1H, $^3J_{HH}$=1.7 Hz, $^3J_{HH}$=2.5 Hz, H$_4$);

$^{13}$C NMR/DMSO-d$_6$: δ 141.28 (C3), 138.57 (C1), 135.27 (C11), 134.12 (C9), 127.92 (C5), 127.54 (C12), 121.75 (C2 and C6), 119.36 (C7 and C8), 118.68 (C10), 108.12 (C4);
GC/MS: Rt=22.49 min, M/Z=210, purity=100%;
Rf=0.22 (eluent: diethyl ether/methanol, 90/10).

Example 1.9

Preparation of 1H, 'H-1,1'-p-phenylene-bis-pyrazole

Example 1.8 was repeated, replacing the 1-(4'-bromophenyl)-1H-imidazole with 1-(4'-bromophenyl)-1H-pyrazole (2.4 mmoles, 535 mg).
Pale yellow crystals were obtained which could be rendered colourless by re-crystallisation from chloroform.
The degree of transformation and isolated yield were 100%.
The compound obtained had the following formula:

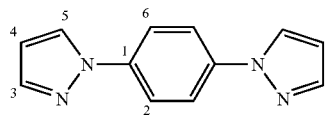

The characteristics were as follows:
M Pt: 180° C. (CHCl$_3$): (Lit: 182° C., CHCl$_3$ obtained by Kauffmann, T; Lexy, H., Chem. Ber. 1980, 113, 2749–2754);
$^1$H NMR/CDCl$_3$ (250 MHz): δ 7.95 (dd, 1H, $^3$J$_{HH}$=2.5 Hz, $^4$J$_{HH}$=0.6 Hz, H$_5$), 7.79 (s, 2H, H$_{2,6}$), 7.74 (dd, 1H, $^3$J$_{HH}$=1.6 Hz, $^4$J$_{HH}$=0.6 Hz, H$_3$), 6.49 (dd, 1H, $^3$J$_{HH}$=1.6 Hz, $^3$J$_{HH}$=2.5 Hz, H$_4$);
$^{13}$C NMR/CDCl$_3$: δ 141.31 (C3), 138.41 (C1), 126.74 (C5), 120.04 (C2 and C6), 107.90 (C4);
GC/MS: Rt=21.28 min, M/Z=210, purity=98%;
Rf=0.38 (eluent: dichloromethane/ethyl acetate, 90/10).

Example 1.10

Preparation of 1-trans-styryl-1H-pyrazole

Operating protocol A (82° C., 24 hours) was followed using 117 mg of Chxn-Py-Al (0.4 mmoles), 387 µl of β-bromostyrene (3 mmoles trans/cis=91/9), 136 mg of pyrazole (2 mmoles) and 1.2 ml of acetonitrile.
The residue obtained was purified by silica gel chromatography (eluent: hexane/dichloromethane 100/0 to 50/50).
327 mg of a pale yellow solid was obtained, corresponding to a yield of 96% by weight.
The compound obtained had the following formula:

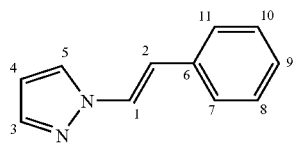

The characteristics were as follows:
M Pt: 53° C.;
$^1$H NMR/CDCl$_3$ (250 MHz): δ 7.66–7.67 (m, 2H, H$_{3,5}$), 7.52 (d, 1H, $^3$J$_{HH}$=14.5 Hz, H$_1$), 7.22–7.48 (m, 5H, H$_{7-11}$), 7.06 (d, 1H, $^3$J$_{HH}$=14.5 Hz, H$_2$), 6.40 (m, 1H, H$_4$). The value of the coupling constant $^3$J$_{H1H2}$ proves that the phenyl and pyrazolyl substituents of the ethylenic bond are located in the trans position. The coupling constants $^4$J$_{H3H5}$, $^3$J$_{H3H4}$ and $^3$J$_{H4H5}$ could not be calculated as the signals were perturbed by coupling with the H$_1$ proton.
$^{13}$C NMR/CDCl$_3$: δ 141.13 (C3), 135.09 (C6), 128.89 (C8 and C10), 128.14 (C1), 127.60 (C9), 126.48 (C5), 126.26 (C7 and C11), 116.88 (C2), 107.34 (C4);
GC/MS: Rt=17.05 min, M/Z=170, purity=98%;
Rf=0.22 (eluent: hexane/dichloromethane, 50/50).

Example 1.11

Preparation of 3,5-dimethyl-1-phenyl-1H-pyrazole

Operating protocol A (110° C., 54 hours) was followed using 117 mg of Chxn-Py-Al (0.4 mmoles), 336 µl of iodobenzene (3 mmoles), 192 mg of 3,5-dimethylpyrazole (2 mmoles) and 1.2 ml of DMF. The degree of transformation and selectivity for 5-dimethyl-1-phenyl-1H-pyrazole were 100%.
The residue obtained following the treatment was purified by silica gel chromatography (eluent: hexane/dichloromethane, 100/0 to 10/90).
323 mg of a yellow oil was obtained, corresponding to a yield of 94% by weight.
The compound obtained had the following formula:

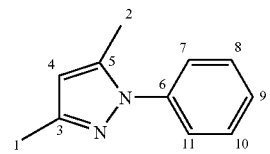

The characteristics were as follows:
$^1$H NMR/CDCl$_3$ (250 MHz): δ 7.25–7.40 (m, 5H, H$_{7,8,9,10,11}$), 5.95 (broad s, 1H, H$_4$), 2.27 (d, $^4$J$_{HH}$=0.8 Hz, 3H, H$_2$), 2.25 (broad s, 3H, HI). Only the coupling constant between the protons of the methyl group located in the 5 position and H$_4$ could be determined. The coupling constant between the protons of the methyl group lcoated in the 3 position and H$_4$ was too small to be read;
$^{13}$C NMR/CDCl$_3$: δ 148.86 (C3), 140.00 (C6), 139.28 (C5), 128.93 (C8 and C10), 127.14 (C9), 124.69 (C7 and C11), 106.92 (C4), 13.48 (C2), 12.31 (C1) [De la Hoz, A; Pardo, M C; Elguero, J; Fruchier, A; Magn. Reson. Chem. 1989, 27, 603–606].
GC/MS: Rt=15.30 min, M/Z=172, purity=99%;
Rf=0.17 (eluent: dichloromethane).

Example 1.12

Preparation of 3,5-dimethyl-1-phenyl-1H-pyrazole

Operating protocol A (110° C., 24 hours) was followed using 117 mg of Chxn-Py-Al (0.4 mmoles), 336 µl of iodobenzene (3 mmoles), 192 mg of 3,5-dimethylpyrazole (2 mmoles) and 1.2 ml of DMF.
The degree of transformation and selectivity for 5-dimethyl-1-phenyl-1H-pyrazole were 75%.

The compound obtained had the following formula:

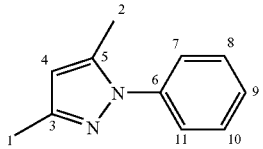

Example 1.13

Preparation of 1-phenyl-1H-pyrazole

Operating protocol A (82° C., 48 hours) was followed using 117 mg of Chxn-Py-Al (0.4 mmoles), 211 µl of bromobenzene (2 mmoles), 204 mg of imidazole (3 mmoles) and 1.2 ml of acetonitrile.

The yellow oil obtained following treatment was purified by silica gel chromatography (eluent: dichloromethane/ethyl acetate, 100/0 to 50/50).

A pale yellow oil corresponding to 1-phenyl-1H-imidazole was obtained in a yield of 80% and had formula:

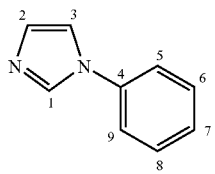

The characteristics were as follows:
H NMR/CDCl$_3$:δ (Collman, J P; Zhong, M; Org. Lett. 2000, 2, 1233–1236, Supporting Information) 7.84 (dd, 1H, $^4J_{HH}$=1.3 Hz, $^4J_{HH}$=1.0 Hz, H$_1$), 7.43–7.53 (m, 2H, H$_{6,8}$), 7.32–7.41 (m, 3H, H$_{5,7,9}$), 7.28 (t, 1H, $^3J_{HH}$=1.3 Hz, $^4J_{HH}$=1.3 Hz, H$_3$), 7.19 (dd, 1H, $^3J_{HH}$=1.3 Hz, $^4J_{HH}$=1.0 Hz, H$_2$);
$^{13}$C NMR/acetone-d$_6$: δ 138.46 (C4), 136.37 (C1), 131.16 (C2), 130.77 (C6 and C8), 127.88 (C7), 121.69 (C5 and C9), 118.77 (C3);
GC/MS: Rt=14.76 min, M/Z=144, purity=100%;
Rf=0.17 (eluent: dichloromethane/ethyl acetate, 50/50).

Example 1.14

Preparation of 1-(4'-trifluoromethylphenyl-1H-imidazole

General procedure A (82° C., 48 hours) was followed using 72 mg of cuprous oxide (0.5 mmoles), 585 mg of Chxn-Py-Al (2 mmoles), 1.40 ml of 4-bromotrifluormethylbenzene (10 mmoles), 1.02 g of imidazole (15 mmoles), 5.86 g of caesium carbonate (18 mmoles) and 6 ml of acetonitrile.

The residue obtained was purified by silica gel chromatography (eluent: hexane/dichloromethane, 100/0 to 0/100).

359 mg of a pale yellow solid was obtained in a yield of 85%.

The compound obtained had the following formula:

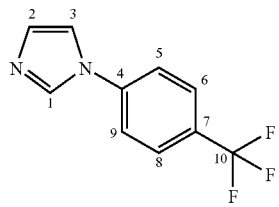

The characteristics were as follows:
MPt: 70° C.;
$^1$H NMR/CDCl$_3$:δ 7.90 (wide s, 1H, H$_1$), 7.72 (m, 2H, H$_{5,9}$), 7.49 (m, 2H, H$_{6,8}$), 7.31 (wide s, 1H, H$_3$), 7.22 (s, 1H, H$_2$);
$^{13}$C NMR$_1$ DMSO-d$_6$: δ 8.43 (wide s, 1H, Hi), 7.85–7.95 (m, 5H, H$_{3,5,6,8,9}$), 7.22 (s, 1H, H$_2$);
$^{13}$C NMR/CDCl$_3$: 139.99 (C4), 135.52 (C1), 131.20 (C2),129.47 (q, J$_{CF}$=33.2 Hz, C7), 127.23 (q, $^3$J$_{CF}$=3.8 Hz, C6 and C8), 123.63 (q, $^1$J$_{CF}$=272.1 Hz, C10), 121.25 (C5 and C9), 118.26 (C3);
$^{19}$F NMR/CDCl$_3$: δ −62.92 (CF$_3$);
GC/MS: Rt=14.82 min, M/Z=212, purity=98%;
Rf=0.20 (eluent: dichloromethane).

Example 1.15

Preparation of 1-phenyl-1H-indole

Operating protocol A (82° C., 24 hours) was followed using 117 mg of Chxn-Py-Al (0.4 mmoles), 224 µl of iodobenzene (2 mmoles), 351 mg of indole (3 mmoles) and 1.2 ml of acetonitrile.

The degree of transformation and selectivity for 1-phenyl-1H-indole were 99.5%.

The red oil obtained following treatment was purified by silica gel chromatography (eluent: hexane/dichloromethane, 100/0 to 50150).

A yellow-green oil was obtained in a yield of 92%.
The compound obtained had the following formula:

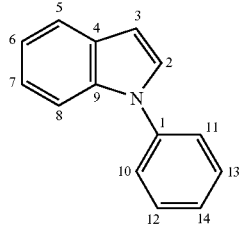

The characteristics were as follows:
$^1$H NMR/CDCl$_3$:δ 7.74–7.80 (m, 1H, H$_5$), 7.62–7.68 (m, 1H, H$_8$), 7.51–7.58 (m, 4H, H$_{10,11,12,13}$), 7.34–7.47 (m, 1H, H$_{14}$), 7.40 (d, $^3$J$_{HH}$=3.3 Hz, 1H, H$_2$); 7.20–7.33 (m, 2H, H$_{6,7}$), 6.76 (dd, 1H, $^3$J$_{H3H2}$=3.3 Hz, $^3$J$_{H3H8}$=0.9 Hz, H$_3$). The attributions were made by means of a COSY H—H experiment.
$^{13}$C NMR/CDCl$_3$: 139.90 (C1), 135.93 (C9), 129.67 (C10 and C11), 129.41 (C4), 128.02 (C14), 126.50 (C2), 124.44 (C12 and C13), 122.43 (C6), 121.21 (C5), 120.43 (C7), 110.58 (C8), 103.65 (C3).
GC/MS: M/Z=193, purity=100%;
Rf=0.23 (eluent: hexane).

Example 1.16

Preparation of 1-phenyl-1H-indole

Operating protocol A (50° C., 74 hours) was followed using 117 mg of Chxn-Py-Al (0.4 mmoles), 224 µl of iodobenzene (2 mmoles), 351 mg of indole (3 mmoles) and 1.2 ml of acetonitrile.

The degree of transformation and selectivity for 1-phenyl-1H-indole was 99%.

The compound obtained had the following formula:

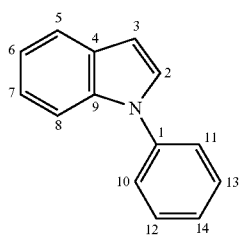

Example 1.17

Preparation of 1-phenyl-1H-1,2,41 triazole

Operating protocol A (82° C., 48 hours) was followed using 117 mg of Chxn-Py-Al (0.4 mmoles), 336 µl of iodobenzene (3 mmoles), 138 mg of 1,2,4-triazole (2 mmoles), 1.042 g of caesium carbonate (3.2 mmoles) and 1.2 ml of DMF.

The degree of transformation and selectivity were 100% and 98% respectively.

The residue obtained following treatment was purified by silica gel chromatography (eluent: hexane/dichloromethane, 100/0 to 50/50).

264 mg of a dark yellow solid was obtained in a yield of 91%.

Pale yellow needles were obtained after re-crystallisation from chloroform.

The compound obtained had the following formula:

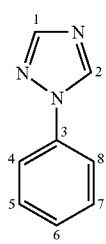

The characteristics were as follows:

MPt: 46° C. (CHCl$_3$) (Lit: 46–47° C. given by Micetich, R G; Spevak, P; Hall, T W; Bains, B K; Heterocycles 1985, 23, 1645–1649);

$^1$H NMR/CDCl$_3$:δ 8.52 (wide s, 1H, H$_1$), 8.04 (wide s, 1H, H$_2$), 7.53–7.65 (m, 2H, H$_{4,8}$), 7.26–7.51 (m, 3H, H$_{5,6,7}$);

$^{13}$C NMR/CDCl$_3$: δ 152.55 (C1), 140.88 (C2), 139.96 (C3), 129.73 (C5 and C7), 128.15 (C6), 119.99 (C4 and C8);

GC/MS: Rt=14.02 min, M/Z=145, purity=100%;

Rf=0.21 (eluent: dichloromethane/ethyl acetate, 90/10).

Example 1.18

Preparation of 1-phenyl-1H-[1,2,4]triazole

Operating protocol A (82° C., 24 hours) was followed using 117 mg of Chxn-Py-Al (0.4 mmoles), 336 µl of iodobenzene (3 mmoles), 138 mg of 1,2,4-triazole (2 mmoles), 1.042 g of caesium carbonate (3.2 mmoles) and 1.2 ml of DMF.

The degree of transformation and selectivity were 79% and 99% respectively.

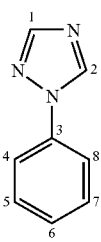

Example 1.19

Preparation of 1-phenyl-1H-[1,2,4]triazole

Example 1.18 was repeated, operating at 50° C. (72 hours). The degree of transformation and selectivity for 1-phenyl-1H-[1,2,4-triazole] were 75% and 99% respectively.

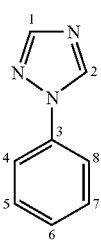

Example 1.20

Preparation of 1-phenyl-1H-pyrrole

Operating protocol C (50° C., 4 days) was followed using 117 mg of Chxn-Py-Al (0.4 mmoles), 269 µl of iodobenzene (2.4 mmoles), 208 µl of pyrrole (2 mmoles) and 1.2 ml of acetonitrile.

The residue obtained was purified by silica gel chromatography (eluent: hexane).

The yield and degree of transformation of 1-phenyl-1H-pyrrole were 100%.

The compound obtained had the following formula:

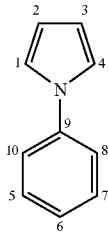

The characteristics were as follows:

MPt: 62° C. (Lit: 62° C. obtained by Dumoulin, H; Rauly, S; Robba, M; J. Heterocycl. Chem. 1995, 32, 1703–1707);

$^1$H NMR/CDCl$_3$:δ 7.50–7.60 (m, 4H, H$_{5,7,1,10}$), 7.38 (m, 1H, H$_6$), 7.26 (m, 2H, H$_{1,4}$), 6.54 (m, 2H, H$_{2,3}$);

$^{13}$C NMR/CDCl$_3$: δ 140.96 (C9), 129.71 (C5 and C7), 125.74 (C6), 120.64 (C8 and C10), 119.44 (C1 and C4), 110.68 (C2 and C3);

GC/MS: Rt=12.75 min, M/Z=143, purity=99%;

Rf=0.33 (eluent: hexane).

Example 1.21

Preparation of 1-phenyl-1H-pyrrole

Operating protocol C (82° C., 4 days) was followed using 117 mg of Chxn-Py-Al (0.4 mmoles), 253 µl of bromobenzene (2.4 mmoles), 208 µl of pyrrole (2 mmoles) and 1.2 ml of acetonitrile.

The residue obtained was purified by silica gel chromatography (eluent: hexane).

The degree of transformation of 1-phenyl-1H-pyrrole was 70%.

The compound obtained had the following formula:

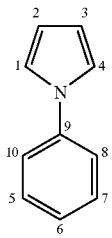

Example 1.22

Preparation of 1-(4'-aminophenyl)-1H-pyrazole

General procedure B (82° C., 42 hours) was followed using 117 mg of Chxn-Py-Al (0.4 mmoles), 516 mg of 4-bromoaniline (3 mmoles), 136 mg of pyrazole (2 mmoles) and 1.2 ml of acetonitrile.

The brown oil obtained after the filtration step was purified directly by alumina chromatography (eluent: hexane/dichloromethane, 100/0 to 50/50).

290 mg of an orange solid was obtained, corresponding to a yield of 91%.

The treatment and analyses were carried out as quickly as possible protected from the light as there was a risk that the compound would decompose.

The compound obtained had the following formula:

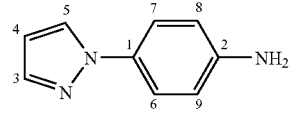

The characteristics were as follows:

MPt: 42–43° C.;

$^1$H NMR/CDCl$_3$ (250 MHz):δ 7.75 (dd, 1H, $^3$J$_{HH}$=2.4 Hz, $^4$J$_{HH}$=0.5 Hz, H$_5$), 7.66 (dd, 1H, $^3$J$_{HH}$=1.8 Hz, ??=0.5 Hz, H$_3$), 7.40 (m, 2H, H$_{6,7}$), 6.66 (m, 2H, H$_{8,9}$), 6.38 (dd, 1H, $^3$J$_{HH}$=?? Hz, $^3$J$_{HH}$=2.4 Hz, H$_4$) 3.79 (s, 2H, NH$_2$). Purity=98%;

$^{13}$C NMR/CDCl$_3$: δ 145.47 (C2), 140.22 (C3), 132.31 (C1), 126.80 (C5), 121.10 (C6, C7), 115.43 (C8, C9), 106.83 (C4);

GC/MS: Rt=17.77 min, M/Z=159;

Rf=0.17 (eluent: dichloromethane/ethyl acetate, 95/5, silica) or 0.17 (eluent: dichloromethane/hexane, 50/50, alumina).

Example 1.23

Preparation of 1-methyl-4-(1H-pyrazol-1'-yl)-1H-pyrazole

The preceding example was repeated, using pyrazole and 1-methyl-4-bromopyrazole.

The compound obtained had the following formula:

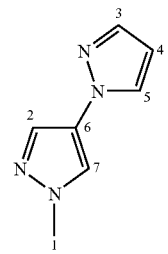

The characteristics were as follows:

M.Pt: 63–64° C.;

$^1$H NMR/acetone-d$_6$ (250 MHz): δ 8.00 (dd, 1H, $^3$J$_{HH}$=2.4 Hz, $^4$J$_{HH}$=0.65 Hz, H$_5$), 8.00 (d, 1H, $^4$J$_{HH}$=0.75 Hz, H$_7$), 7.77 (d, 1H, $^4$J$_{HH}$=0.75 Hz, H$_2$), 7.60 (dd, 1H, $^3$J$_{HH}$=1.85 Hz, $^4$J$_{HH}$=0.65 Hz, H$_3$), 6.41 (dd, H, $^3$J$_{HH}$=1.85 Hz, $^3$J$_{HH}$=24H$_1$H$_4$), 3.94 (s, 3H, H$_1$);

$^{13}$C NMR/CDCl$_3$: δ 140.34 (C3), 130.55 (C5), 127.98 (C2), 126.30 (C6), 121.93 (C7), 106.68 (C4), 39.51 (C1);

GC/MS: Rt=14.13 min, M/Z=148, purity=99%;

FAB+ (NBA matrix): 149 (100%, M+H$^+$), 55 (24%), 148 (22%), 69 (20%, pyrazole+H$^+$), 297 (3%, 2M+1);

HRMS: Calculated for C$_7$H$_9$N$_4$(M$^+$+H): 149.0827. Found: 149.0819;

Rf: 0.28 (eluent: dichloromethane/methanol, 98/2).

Example 1.24

Preparation of 1-phenyl-3-trifluoromethyl-5-(p-tolyl)-1H-pyrazole

This compound was isolated by silica gel chromatography following arylation of 3-trifluoromethyl-5-(p-tolyl)-1H pyrazole using iodobenzene as described in Example 1.1.

The compound obtained had the following formula:

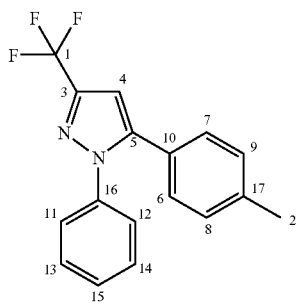

The characteristics were as follows:

$^1$H NMR/acetone-d$_6$: δ 7.39–7.46 (m, 3H, H$_{13,14,15}$), 7.33–7.38 (m, 2H, H$_{11,12}$), 7.19 (m, 4H, H$_{6-9}$), 6.94 (q, 1H, $^4J_{HF}$=0.6 Hz, H$_4$), 2.32 (s, 3H, H$_2$);

$^{13}$C NMR/acetone-d$_6$: δ 146.01 (C5), 143.32 (q, $^2J_{CF}$=38.0 Hz, C3), 140.48 (C17), 139.95 (C16), 130.16 (C13 and C14), 129.99 (C8 and C9), 129.65 (C6 and C7), 129.44 (C15), 127.20 (C10), 126.51 (C11 and C12), 122.64 (q, $^1J_{CF}$=268.3 Hz, C1), 106.01 (q, $^3J_{CF}$=1.9 Hz, C4), 21.20 (C2). Carbons 6–9 have similar chemical displacements, which agrees with the fact that the signals for protons 6–9 are superimposed;

$^{19}$F NMR/acetone-d$_6$: δ −63.05 (d, $^4J_{HF}$=0.6 Hz), purity=99.8%;

GC/MS: Rt=20.54 min, M/Z=302, purity>99.5%;

Rf: 0.30 (eluent: hexane/dichloromethane, 80/20).

Example 1.25

Preparation of 1-phenyl-3-(i)-tolyl)-5-trifluoromethyl-1H-pyrazole

As described for the preceding example, this compound was isolated by arylation of 3-trifluoromethyl-5-(p-tolyl)-1H pyrazole using iodobenzene.

The compound obtained had the following formula:

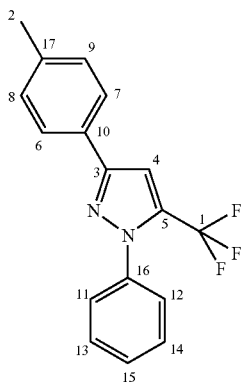

The characteristics were as follows:

$^{13}$C NMR/acetone-d$_6$: δ 152.44 (C3), 140.12 (q, $^2J_{CF}$=18.2 Hz, C5), 139.31 (C16), 134.48 (C17), 130.26 (C8, C9 and C15), 130.06 (C13 and C14), 127.21 (C10), 126.64 (q, $^6J_{CF}$=0.4 Hz, C6 and C7) 126.48 (C11 and C12), 120.95 (q, $^1J_{CF}$=283H, C1) 106.01 (q $^3J_{CF}$=2.6 Hz, C4), 21.23 (C2);

$^{19}$F NMR acetone-d$_6$: δ −58.51(s);

GC/MS: Rt=21.16 min, m/z=302, purity=98%;

Rf: 0.34 (eluent: hexane/dichloromethane, 80/20).

Example 1.26

Preparation of 5-(3-chlorosulphonl-4-methylphenyl)-1-phenyl-3-trifluoromethyl-1H-pyrazole As described for in Example 1.24, this compound was obtained by arylation of 5-(3-chlorosulphonyl-4-methylphenyl)-3-trifluoromethyl-1H pyrazole using iodobenzene.

The compound obtained had the following formula:

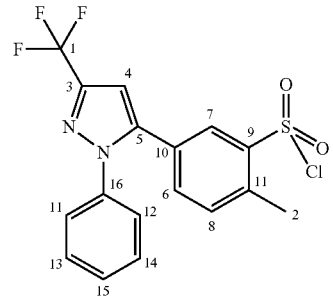

The characteristics were as follows:

$^1$H NMR/CDCl$_3$: δ 7.94 (m, 1H, H$_7$), 7.40–7.47 (m, 3H), 7.37–7.39 (m, 2H), 7.27–7.35 (m, 2H), 6.87 (m, 1H, H$_4$), 2.78 (s, 3H, H$_2$). Purity: 95%;

GC/MS: Rt=25.92 min, M/Z=400 and 402;

Rf: 0.24 (eluent: hexane/dichloromethane, 80/20).

Example 2

N-arylation of Amides, Carbamates and Derivatives

General Operating Protocol

The following are successively introduced into a 35 ml Schlenk tube placed in a nitrogen atmosphere:
- cuprous oxide (0.1 mmoles);
- ligand (0.4 mmoles);
- nucleophilic compound (3 mmoles);
- a base (4 mmoles);
- 2 mmoles of arylation agent;
- and 1.2 ml of acetonitrile or DMF The mixture is placed in an oil bath at a temperature of 82° C. and stirred for 24 hours. After this period, the mixture is diluted with ethyl ether or dichloromethane.

Determination of Isolated Yield:

After the period, the reaction mixture is diluted with 25 ml of dichloromethane, filtered through celite, concentrated completely under reduced pressure then taken up in 50 ml of dichloromethane.

This organic phase is extracted with distilled water (2×20 ml).

The aqueous phase is extracted again with 20 ml of dichloromethane.

The total organic phase is washed with a saturated aqueous sodium chloride solution (2×20 ml), dried over MgSO$_4$, filtered and concentrated under reduced pressure.

The residue obtained is purified by silica gel chromatography (35–70 μm).

Determination of Degree of Transformation:

After the period, 65 μl of 1,3-dimethoxybenzene (internal reference) is introduced into the cooled reaction medium, which is then diluted with 5 ml of diethyl ether or dichloromethane, depending on the solubility of the products to be analysed.

An aliquot is then removed, filtered through celite, eluting with diethyl ether or dichloromethane, extracted three times with distilled water then analysed by gas chromatography.

Example 2.1

Preparation of 3-ohenyloxazolidin-2-one 14.4 mg of cuprous oxide (0.1 mmoles), 117 mg of Chxn-Py-Al (0.4 mmoles), 263 mg of oxazolidin-2-one (3 mmoles), 1.043 g of caesium carbonate (3.2 mmoles) and 600 mg of ground and activated 3 A molecular sieve (K$_n$Na$_{12,-n}$[(AlO$_2$)$_{12}$(SiO$_2$)$_{12}$]) were successively introduced into a 35 ml Schlenk tube that had been oven dried at 100 1C and provided with a magnetic stirrer (12×4.5 mm) and under a nitrogen atmosphere.

The Schlenk tube was purged under vacuum then refilled with nitrogen.

224 μl of iodobenzene (2 mmoles) then 1.2 ml of DMF were then added using syringes.

The reactor was placed in an oil bath at a temperature of 82° C. and stirred for a period of 24 hours.

The degree of transformation of 3-phenyloxazolidin-2-one was 99.7% and the selectivity reached 100%.

After the period, the reaction mixture was diluted with 25 ml of dichloromethane, filtered through celite, concentrated completely under reduced pressure then taken up in 50 ml of dichloromethane.

This organic phase was extracted with distilled water (2×20 ml).

The aqueous phase is extracted again with 20 ml of dichloromethane.

The total organic phase was washed with a saturated aqueous sodium chloride solution (2×20 ml), dried over MgSO$_4$, filtered and concentrated under reduced pressure.

The residue obtained was purified by silica gel chromatography (eluent: hexane/dichloromethane, 50/50 to 0/100).

316 mg of a colourless solid was obtained, corresponding to a yield of 97%.

The compound obtained had the following formula:

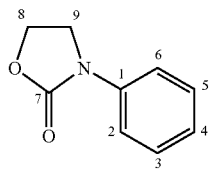

The characteristics were as follows:
M.Pt: 120° C. (Lit: 120–121° C., given by Gulbins, E; Hamann, K; Chem. Ber. 1966, 99, 55–61);
$^1$H NMR/CDCl$_3$: δ 7.48–7.53 (m, 2H, H$_{3,5}$), 7.30–7.38 (m, 2H, H$_{2,6}$), 7.07–7.15 (m, 1H, H$_4$), 4.40 (m, 2H, H$_8$, $^3$J$_{HH}$=8.00 Hz), 3.97 (m, 2H, H$_9$, $^3$J$_{HH}$=8.0 Hz);
$^{13}$C NMR/CDCl$_3$: δ 155.34 (C7), 138.30 (C1), 129.04 (C3 and C5), 124.01 (C4), 118.22 (C2 and C6), 61.37 (C8), 45.14 (C9);
GC/MS: Rt=18.25 min, M/Z=163, purity=1100%;
Rf: 0.29 (eluent: dichloromethane).

Example 2.2

Preparation of 3-phenyloxazolidin-2-one

Example 2.1 was repeated, heating for 96 h at 50° C.
The degree of transformation of 3-phenyloxazolidin-2-one was 99.6% and the selectivity reached 100%.

Example 2.3

Preparation of 1-phenyl-1H-pyridin-2-one

Example 2.1 was repeated, using 72 mg of cuprous oxide (0.5 mmoles), 584 mg of Chxn-Py-Al (2 mmoles), 951 mg of 2-hydroxypyridine (0 mmoles), 6.52 g of caesium carbonate (20 mmoles), 3 g of ground and activated 3 Å molecular sieve, 1.68 ml of iodobenzene (15 mmoles) and 6 ml of acetonitrile.

The degree of transformation of 1-phenyl-1H-pyridin-2-one was 98%.

The residue obtained was purified by silica gel chromatography (eluent: hexane/dichloromethane/ethyl acetate, 100/0/0 to 0/100/0 then 0/100/0 to 0/80/20).

1.54 g of a yellow solid was obtained, corresponding to a yield of 90%.

The compound obtained had the following formula:

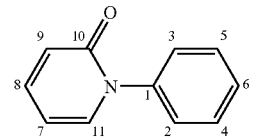

The characteristics were as follows:
M.Pt: 127° C. (Lit: 129° C., diisopropyl ether, given by Ukita, T; Sugahara, M; Chem. Pharm. Bull. 1997, 45, 719–721);
$^1$H NMR/DMSO-d$_6$: δ 7.59–7.66 (m, 1H, HI,), 7.36–7.56 (m, 6H, H$_{2-6,8}$), 6.48 (m, 1H, H$_9$), 6.31 (m, 1H, H$_7$);
$^{13}$C NMR/CDCl$_3$: δ 162.41 (C10), 140.97 (C1), 139.88 (C11), 138.01 (C8), 129.34 (C4 and C5), 128.48 (C6), 126.54 (C2 and C3), 121.91 (C9), 105.93 (C7);
GC/MS: Rt=18.11 min, M/Z=171, purity=99%;
Rf: 0.14 (eluent: dichloromethane/ethyl acetate, 90/10).

Example 2.4

Preparation of benzanilide (N-phenylbenzamide)

Example 2.1 was repeated, replacing the oxazolidin-2-one with 363 mg of benzamide (3 mmoles) and taking the reaction time to 48 h.

The degree of transformation of N-phenylbenzamide was 96% and the selectivity reached 100%.

The residue obtained was purified by silica gel chromatography (eluent: hexane/dichloromethane, 50/50 to 100/0).

359 mg of a colourless solid was obtained, corresponding to a yield of 91%.

The compound obtained had the following formula:

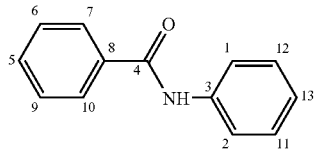

The characteristics were as follows:

M.Pt: 164° C. (Lit: 163° C., EtOH, given by Goswami, B N; Borthakur, N, Ghosh, A C; J. Chem. Research (S), 1998, 268–269);

$^1$H NMR/CDCl$_3$: δ 7.88 (wide s, 1H, NH), 7.86 (m, 2H, H$_{7,10}$), 7.64 (m, 2H, H$_{6,9}$), 7.32–7.58 (m, 5H, H$_{1,2,5,11,12}$) 7.15 (m, 1H, H$_{13}$). Purity=99%;

$^{13}$C NMR/CDCl$_3$: δ 165.81 (C4), 137.96 (C3), 135.03 (C8), 131.83 (C5), 129.09 (C11 and C12), 128.78 (C7 and C10), 127.04 (C6 and C9), 124.58 (C13), 120.27 (C1 and C2);

GC/MS: Rt=20.76 min, M/Z=197;

Rf: 0.45 (eluent: dichloromethane).

Example 2.5

Preparation of 1-phenylpyrrolidin-2-one

Example 2.1 was repeated, replacing the oxazolidin-2-one with 152 μl of pyrrolidin-2-one (2 mmoles) and operating with 336 μl of iodobenzene (3 mmoles), the latter being added at the same time as the pyrrolidin-2-one.

The reaction time was taken to 40 h.

The degree of transformation and selectivity for 1-phenylpyrrolidin-2-one were 100%.

The residue obtained was purified by silica gel chromatography (eluent: hexane/dichloromethane/ethyl acetate, 50/50/0 to 0/95/5).

297 mg of a colourless solid was obtained, corresponding to a yield of 92%.

The compound could also be isolated by re-crystallising the residue obtained from the solvent extraction steps from ethanol rather than using silica chromatography.

265 mg of a beige solid was obtained, corresponding to a yield of 82%.

The compound obtained had the following formula:

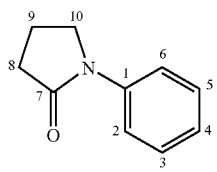

The characteristics were as follows:

M.Pt: 69–70° C. (Lit: 70° C., diisopropyl ether, given by Ukita, T; Sugahara, M; Chem. Pharm. Bull. 1997, 45, 719–721);

$^1$H NMR/CDCl$_3$: δ 7.58–7.63 (m, 2H, H$_{2,6}$), 7.32–7.40 (m, 2H, H$_{3,5}$), 7.13–7.18 (m, 1H, H$_4$), 3.87 (m, 2H, H$_{10}$) 2.61 (m, 2H, H$_8$), 2.08–2.23 (m, 2H, H$_9$);

$^{13}$C NMR/CDCl$_3$: δ 174.20 (C7), 139.43 (C1), 128.81 (C2 and C6), 124.48 (C4), 119.96 (C3 and C5), 48.78 (C10), 32.76 (C8), 18.03 (C9);

GC/MS: Rt=17.38 min, M/Z=161, Purity=99%;

Rf: 0.53 (eluent: dichloromethane/ethyl acetate, 80/20).

Example 2.6

Preparation of N-phenylbenzenesulphonamide

Example 2.1 was repeated, using 14.4 mg of cuprous oxide (0.1 mmoles), 117 mg of Chxn-Py-Al (0.4 mmoles), 472 mg of benzenesulphonamide (3 mmoles), 224 μl of iodobenzene (2 mmoles), 1.04 g of caesium carbonate (3.2 mmoles), 600 mg of ground and activated 3 Å molecular sieve and 1.6 ml of DMF.

The reaction time was taken to 48 h.

The degree of transformation of N-phenylbenzenesulphonamide was 95%.

After this reaction period, the reaction mixture was diluted with 25 ml of dichloromethane/methanol and filtered through celite.

The residue obtained was purified by silica gel chromatography (eluent: hexane/dichloromethane, 90/10 to 5/95).

411 mg of a colourless solid was obtained, corresponding to a yield of 88%.

The compound obtained had the following formula:

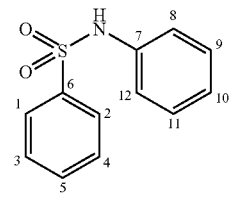

The characteristics were as follows:

M.Pt: 109–110° C. (Lit: 110° C., given by Hellwinkel, D; Supp, M; Chem. Ber. 1976, 109, 3749–3766);

$^1$H NMR/CDCl$_6$: δ 7.78–7.88 (m, 2H, H$_{1,2}$), 7.79 (broad s, 1H, NH), 7.35–7.50 (m, 3H, H$_{3,5}$), 7.07–7.25 (m, 5H, H$_{8-12}$);

$^{13}$C NMR/CDCl$_3$: δ 138.89 (C6), 136.58 (C7), 133.10 (C5), 129.34 (C3 and C4), 129.10 (C9 and C11), 127.29 (C1 and C2), 125.33 (C10), 121.55 (C8 and C12);

GC/MS: Rt=21.54 min, M/Z=233, purity=99%;

Rf: 0.36 (eluent: dichloromethane).

Example 3

Arylation of Ethers

General Operating Protocol

The following are successively introduced into a 35 ml Schlenk tube placed in a nitrogen atmosphere:

Cuprous oxide (0.1 mmoles);
ligand (0.4 mmoles);
nucleophilic compound (2 mmoles);
a base (4 mmoles);
3 mmoles of arylation agent;
and 1.2 ml of acetonitrile.

The mixture is placed in an oil bath at a temperature of 82° C. and stirred for 24 hours.

Determination of Isolated Yield:

After the period, the reaction mixture is diluted with 25 ml of dichloromethane, filtered through celite, concentrated completely under reduced pressure then taken up in 50 ml of dichloromethane.

This organic phase is extracted with distilled water (2×20 ml).

The aqueous phase is extracted again with 20 ml of dichloromethane.

The total organic phase is washed with a saturated aqueous sodium chloride solution (2×20 ml), dried over MgSO$_4$, filtered and concentrated under reduced pressure.

The residue obtained is purified by silica gel chromatography (35–70 μm).

Determination of Degree of Transformation:

After the period, 65 μl of 1,3-dimethoxybenzene (internal reference) is introduced into the cooled reaction medium, which is then diluted with 5 ml of diethyl ether or dichloromethane, depending on the solubility of the products to be analysed.

An aliquot is then removed, filtered through celite, eluting with diethyl ether or dichloromethane, extracted three times with distilled water then analysed by gas chromatography.

Example 3.1

Preparation of Diphenyl Ether 14.4 mg of cuprous oxide (0.1 mmoles), 117 mg of Chxn-Py-Al (0.4 mmoles), 188 mg of phenol (2 mmoles), 1.303 g of caesium carbonate (4 mmoles) and 600 mg of ground and activated 3 Å molecular sieve (K$_n$Na$_{12-n}$[(AlO$_2$)$_{12}$(SiO$_2$)12]) were successively introduced into a 35 ml Schlenk tube that had been oven dried at 100° C. and provided with a magnetic stirrer (12×4.5 mm) and under a nitrogen atmosphere.

The Schlenk tube was purged under vacuum then refilled with nitrogen.

336 μl of iodobenzene (3 mmoles) then 1.2 ml of acetonitrile were added using syringes.

The reactor was placed in an oil bath at a temperature of 82° C. and stirred for a period of 24 hours.

The degree of transformation and the selectivity for diphenyl ether were 100%.

After this period, the reaction mixture was diluted with 25 ml of dichloromethane, filtered through celite, concentrated completely under reduced pressure then taken up in 50 ml of dichloromethane.

This organic phase was extracted with distilled water (2×20 ml).

The aqueous phase was extracted again with 20 ml of dichloromethane.

The total organic phase was washed with a saturated aqueous sodium chloride solution (2×20 ml), dried over MgSO$_4$, filtered and concentrated under reduced pressure.

The oily residue obtained after treatment was complete was purified by silica gel chromatography (eluent: hexane).

344 mg of a colourless oil was obtained (corresponding to a yield of 100%), which crystallised out after a few hours in the refrigerator (colourless crystals).

The compound obtained had the following formula:

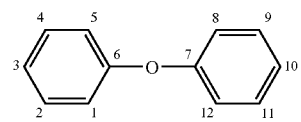

The characteristics were as follows:
M.Pt: 26° C. (Lit: 85° C., given by Byers, C H; Williams, D F; J. Chem. Eng. Data 1987, 32, 344–348);
$^1$H NMR/CDCl$_3$: δ 7.37–7.47 (m, 4H, H$_{2,4,9,11}$), 7.10–7.23 (m, 6H, H$_{1,3,5,10,12}$);
$^{13}$C NMR/CDCl$_3$: δ 157.38 (C6 and C7), 129.88 (C2, C4, C9 and C11), 123.35 (C3 and C10), 119.02 (C1, C5, C8 and C12);
GC/MS: Rt=14.43 min, M/Z=170, purity=99%;
Rf: 0.33 (eluent: hexane).

Example 3.2

Preparation of 4-methoxyphenyl phenyl ether

Example 3.1 was repeated, replacing the phenol with 248 mg of 4-methoxyphenol (2 mmoles) and heating for 28 h at 82° C.

The degree of transformation and the selectivity for 4-methoxyphenyl phenyl ether were 100%.

The orange oil obtained after treatment was complete was purified by silica gel chromatography (eluent: hexane/dichloromethane, 100/0 to 95/5).

380 mg of a colourless oil was obtained, which corresponded to a yield of 95%.

The compound obtained had the following formula:

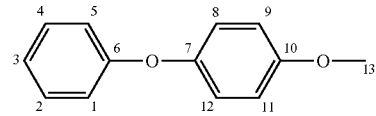

The characteristics were as follows:
$^1$H NMR/CDCl$_3$: δ 7.30–7.39 (m, 2H, H$_{2,4}$), 6.89–7.09 (m, 7H, H$_{1,3,5,8,9,11,12}$), 3.84 (s, 3H, H$_{13}$);
$^{13}$C NMR/CDCl$_3$: δ 158.60 (C6), 155.97 (C10), 150.18 (C7), 129.69 (C2 and C4), 122.49 (C3), 120.91 (C8 and C12), 117.64 (C1 and C5), 114.92 (C9 and C11), 55.67 (C13);
GC/MS: Rt=17.67 min, M/Z=200, purity=95.5%;
Rf: 0.25 (eluent: hexane/dichloromethane, 80/20).

Example 3.3

Preparation of 4-t-butylphenyl phenyl ether

Example 3.1 was repeated, replacing the phenol with 300 mg of 4-t-butylphenol (2 mmoles).

The degree of transformation and the selectivity for 4-t-butylphenyl phenyl ether were 100%.

The oily residue obtained after treatment was complete was purified by silica gel chromatography (eluent: hexane).

430 mg of a colourless oil was obtained (which corresponded to a yield of 95%), which crystallised after a few hours in the refrigerator (colourless crystals).

The compound obtained had the following formula:

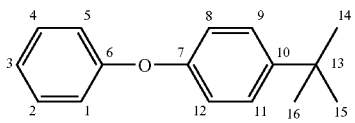

The characteristics were as follows:
M.Pt: 52° C. (Lit: 53–54° C., given Harvey, L; Gleicher, G J; Totherow, W D; Tetrahedron 1969, 25, 5019–5026);
$^1$H NMR/DMSO-$d_6$: δ 7.33–7.41 (m, 4H, $H_{2,4,8,12}$), 7.06–7.14 (m, 1H, $H_3$), 6.91–6.99 (m, 4H, $H_{1,5,9,11}$), 1.27 (s, 9H, $H_{14,15,16}$);
$^{13}$C NMR/DMSO-$d_6$: δ 156.94 (C6), 154.09 (C7), 145.73 (C10), 129.88 (C2 and C4), 126.61 (C9 and C11), 123.05 (C3), 118.21 (C1, C5, C8 and C12), 33.96 (C13), 31.18 (C14, C15 and C16).
GC/MS: Rt=18.50 min, M/Z=226, purity=98.5%;
Rf: 0.36 (eluent: hexane).

Example 3.4

Preparation of 3,5-dimethylphenyl phenyl ether

Example 3.1 was repeated, replacing the phenol with 244 mg of 3,5-dimethylphenol (2 mmoles).
The degree of transformation and the selectivity for 3,5-dimethylphenyl phenyl ether were 100%.
The brown oil obtained after treatment was complete was purified by silica gel chromatography (eluent: hexane).
381 mg of a colourless oil was obtained, which corresponded to a yield of 97%.
The compound obtained had the following formula:

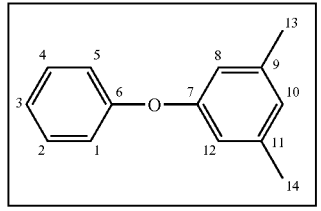

The characteristics were as follows:
$^1$H NMR/CDCl$_3$: δ 7.28–7.42 (m, 2H, $H_{2,4}$), 7.12–7.17 (m, 1H, $H_3$), 7.03–7.14 (m, 2H, $H_{1,5}$), 6.79 (m, 1H, $H_{10}$), 6.69 (m, 2H, $H_{8,12}$), 2.33 (s, 6H, $H_{13,14}$);
$^{13}$C NMR/CDCl$_3$: δ 157.50 (C6), 157.22 (C7), 139.61 (C9 and C11), 129.70 (C2 and C4), 125.04 (C10), 123.02 (C3), 118.89 (C1 and C5), 116.67 (C8 and C12), 21.35 (C13);
GC/MS: Rt=16.87 min, M/Z=198, purity=98%;
Rf: 0.19 (eluent: hexane).

Example 3.5

Preparation of 3,5-dimethylphenyl phenyl ether from bromobenzene

Example 3.3 was repeated, replacing the iodobenzene with bromobenzene (316 µl, 3 mmoles), the acetonitrile with DMF, and heating for 24 h at 110° C.

The degree of transformation of 3,5-dimethylphenyl ether was 70%.
The degree of transformation of 3,5-dimethylphenyl ether was 100% after heating for 72 h under these conditions.

Example 3.6

Preparation of 3,5-dimethylphenyl 4-trifluoromethylphenyl ether

Example 3.1-was repeated, replacing the phenol with 244 mg of 3,5-dimethylphenol (2 mmoles) and the iodobenzene with 294 µl of 4-iodotrifluoromethylbenzene (2.6 mmoles).
The degree of transformation and the selectivity for 3,5-dimethylphenyl 4-trifluoromethylphenyl ether were 100%.
The residue obtained after treatment was complete was purified by silica gel chromatography (eluent: hexane).
506 mg of an orange oil was obtained, which corresponded to a yield of 95%.
The compound obtained had the following formula:

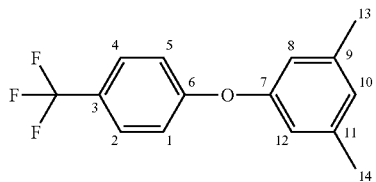

The characteristics were as follows:
$^1$H NMR/CDCl$_3$: δ 7.59 (m, 2H, $H_{2,4}$), 7.06 (m, 2H, $H_{1,5}$), 6.87 (m, 1H, $H_{10}$), 6.71 (m, 2H, $H_{8,12}$), 2.35 (s, 6H, $H_{13,14}$);
$^{13}$C NMR/CDCl$_3$: δ 160.78 (C6), 155.65 (C7), 140.01 (C9 and C11), 127.04 (q, $^3J_{CF}$=3.8 Hz, C2 and C4), 126.25 (C10), 124.59 (q, $^2J_{CF}$=32.7 Hz, C3), 118.92 (q, $^1J_{CF}$=271.1 Hz, C15), 117.78 (C8 and C12), 117.63 (C1 and C5), 21.26 (C13 and C14);
$^{19}$F NMR/CDCl$_3$: δ−62.11 (CF$_3$);
Elemental analysis: Calculated: C: 67.66%; H: 4.92%; F: 21.41%. Found: C: 67.37%; H: 5.03%; F: 21.80%;
GC/MS: Rt=16.71 min, M/Z=266, purity=99%;
IR (CH$_2$Cl$_2$): 3053 (VW, aromatic), 2985 (VW), 1615, 1591 and 1513 (W, aromatic C=C), 1326 (VS, CF$_3$), 1237 (S, C—O), 1169 (S, CF$_3$), 1123 (S), 1066 (S), 840 (W), 748 (VS), 730 (S).
Rf: 0.68 (eluent: hexane).

Example 3.7

Preparation of 3.5-dimethylphenyl 2-methylphenyl ether

Example 3.1 was repeated, replacing the phenol with 244 mg of 3,5-dimethylphenol (2 mmoles) and the iodobenzene with 383 µl of 2-iodotoluene (3 mmoles), and taking the reaction time to 118 hours.
The degree of transformation and the selectivity for 3,5-dimethylphenyl 2-methylphenyl ether were 100%.
The oily residue obtained after treatment was complete was purified by silica gel chromatography (eluent: hexane).
399 mg of a colurless oil was obtained, which corresponded to a yield of 94%.

The compound obtained had the following formula:

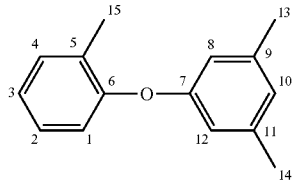

The characteristics were as follows:
$^1$H NMR/CDCl$_3$: δ 7.08–7.33 (m, 3H, H$_{2,3,4}$), 6.95–6.99 (m, 1H, H$_1$), 6.76 (m, 1H, H$_{10}$), 6.61 (m, 2H, H$_{8,12}$), 2.33 (s, 6H, H$_{13,14}$), 2.32 (s, 3H, H$_{15}$) [Buchwald, S L; Marcoux, J-F; Doye, S; J. Am. Chem. Soc. 1997, 119, 10539–10540, Supporting Information);
$^{13}$C NMR/CDCl$_3$: δ 157.94 (C6), 154.69 (C7), 139.55 (C9 and C11), 131.41 (C2), 130.02 (C5), 127.14 (C4), 124.22 (C10), 123.83 (C3), 119.81 (C1), 115.11 (C8 and C12), 21.42 (C13 and C14), 16.30 (C15);
GC/MS: Rt=17.46 min, M/Z=212, purity=99.7%;
Rf: 0.26 (eluent: hexane).

Example 3.8

Preparation of 3.5-dimethylphenyl 4-methoxyphenyl ether

Example 3.1 was repeated, replacing the phenol with 244 mg of 3,5-dimethylphenol (2 mmoles) and the iodobenzene with 655 mg of 4-iodoanisole (2.8 mmoles), the latter being added at the same time as the 3,5-dimethylphenol, and taking the reaction time to 48 hours.

The degree of transformation and the selectivity for 3,5-dimethylphenyl 4-methoxyphenyl ether were 100%.

The residue obtained after treatment was placed in an oven at 100° C. to evaporate off the anisole, then it was purified by silica gel chromatography (eluent: hexane).

420 mg of a colourless oil was obtained, which corresponded to a yield of 92%.

Crystals could be obtained after re-crystallisation from petroleum ether.

The compound obtained had the following formula:

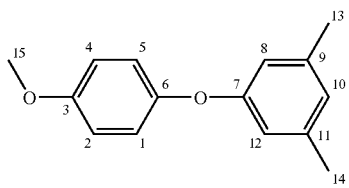

The characteristics were as follows:
M.Pt: 67° C. (Lit: 67° C., given by Walter; Barell-Festschr., Basel 1936, 266–273);
$^1$H NMR/CDCl$_3$: δ 6.99–7.06 (m, 2H, H$_{2,4}$), 6.88–6.99 (m, 2H, H$_{1,5}$), 6.74 (m, 1H, H$_{10}$), 6.64 (m, 2H, H$_{8,12}$), 3.85 (s, 3H, H$_{15}$), 2.32 (s, 6H, H$_{13,14}$);
$^{13}$C NMR/CDCl$_3$: δ 158.52 (C3), 155.76 (C7), 150.26 (C6), 139.45 (C9 and C11), 124.22 (C10), 120.84 (C1 and C5), 115.31 (C2 and C4), 114.77 (C8 and C12), 55.59 (C15), 21.35 (C13 and C14);
GC/MS: Rt=19.77 min, M/Z=228, purity=99%;
Rf: 0.61 (eluent: hexane).

Example 3.9

Preparation of 3,5-dimethylphenyl 4-cyanophenyl ether

Example 3.1 was repeated, replacing the phenol with 244 mg of 3,5-dimethylphenol (2 mmoles) and the iodobenzene with 595 mg of 4-iodobenzonitrile (2.6 mmoles), the latter being added at the same time as the 3,5-dimethylphenol.

The degree of transformation and the selectivity for 3,5-dimethylphenyl 4-cyanophenyl ether were 100%.

The residue obtained after treatment was placed in an oven at 100° C. to evaporate off the benzonitrile then it was purified by silica gel chromatography (eluent: hexane/dichloromethane, 100/0 to 50/50).

415 mg of an orange solid was obtained, which corresponded to a yield of 93%.

The compound obtained had the following formula:

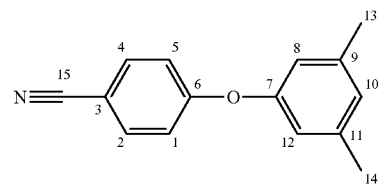

The characteristics were as follows:
M.Pt: 58° C.;
$^1$H NMR/CDCl$_3$: δ 7.53–7.60 (m, 2H, H$_{2,4}$), 6.95–7.00 (m, 2H, H$_{1,5}$), 6.86 (m, 1H, H$_{10}$), 6.68 (m, 2H, H$_{8,12}$), 2.32 (s, 6H, H$_{13,14}$);
$^{13}$C NMR/CDCl$_3$: δ 161.90 (C6), 154.76 (C7), 140.17 (C9 and C11), 134.07 (C2 and C4), 126.86 (C10), 118.92 (C15), 118.03 (C1 and C5), 117.88 (C8 and C12), 105.55 (C3), 21.28 (C13 and C14);
GC/MS: Rt=20.54 min, M/Z=223, purity=100%;
Rf: 0.32 (eluent: hexane/dichloromethane, 50/50).

Example 3.10

Preparation of bis(o-tolyl) Ether

Example 3.1 was repeated, replacing the phenol with 206 µl of o-cresol (2 mmoles) and the iodobenzene with 383 µl of 2-iodotoluene (3 mmoles), the acetonitrile with DMF, and with the nucleophile and the arylation agent being added at the same time as the solvent.

The reaction time was taken to 35 h and the temperature was 110° C.

The degree of transformation and the selectivity for bis(o-tolyl) ether were 100%.

The oily residue obtained after treatment purified by silica gel chromatography (eluent: hexane).

389 mg of a colourless oil was obtained, which corresponded to a yield of 98%.

The compound obtained had the following formula:

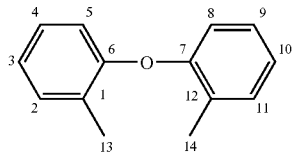

The characteristics were as follows:
$^1$H NMR/CDCl$_3$: δ 7.32 (m, 2H, H$_{2,11}$), 7.04–7.25 (m, 4H, H$_{3,4,9,10}$), 6.81 (m, 2H, H$_{5,8}$), 2.38 (s, 6H, H$_{13,14}$);
$^{13}$C NMR/CDCl$_3$: δ 155.35 (C6 and C7), 131.39 (C4 and C9), 128.90 (C1 and C12), 127.09 (C2 and C11), 123.11 (C3 and C10), 117.74 (C5 and C8), 16.25 (C13 and C14);
GC/MS: Rt=16.10 min, M/Z=198, purity=100%;
Rf: 0.40 (eluent: hexane).

Example 3.11

Preparation of phenyl 2-methylphenyl ether

Example 3.1 was repeated, replacing the phenol with 206 μl of o-cresol (2 mmoles), and with the nucleophile and the arylation agent being added at the same time as the solvent.
The reaction time was taken to 40 h.
The degree of transformation and the selectivity for phenyl 2-methylphenyl ether were 100%.
The oily residue obtained after treatment was purified by silica gel chromatography (eluent: hexane).
343 mg of a colourless oil was obtained, which corresponded to a yield of 93%.
The compound obtained had the following formula:

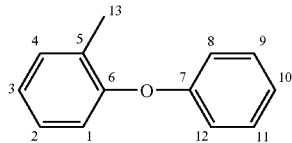

The characteristics were as follows:
$^1$H NMR/CDCl$_3$: δ 7.19–7.35 (m, 3H, H$_{4,9,11}$), 7.00–7.18 (m, 3H, H$_{2,3,10}$), 6.87–6.94 (m, 3H, H$_{1,8,12}$), 2.25 (s, 3H, H$_{13}$);
$^{13}$C NMR/CDCl$_3$: δ 158.08 (C7), 54.60 (C6), 131.60 (C2), 130.14 (C5), 129.81 (C9 and C11), 127.30 (C4), 124.15 (C10), 122.48 (C3), 119.94 (C1), 141 17.44 (C8 and C12), 16.35 (C13);
GC/MS: Rt=15.25 min, M/Z=184, purity=98%;
Rf: 0.36 (eluent: hexane).

Example 3.12

Preparation of 3,5-dimethylphenyl 2-pyridyl ether

General procedure A (110° C., 24 hours) was followed using 117 mg of Chxn-Py-Al (0.4 mmoles), 292 μl of 2-bromopyridine (3 mmoles), 244 mg of 3,5-dimethylphenol (2 mmoles), 600 mg of ground and activated 3 Å molecular sieve and 1.2 ml of DMF.
The oil obtained after the filtering step was oven dried for two hours at 100° C. to evaporate off the 2-pyridylaldehyde then purified by silica gel chromatography (eluent: hexane/dichloromethane, 100/0 to 85/15).
371 mg of a yellow oil was obtained, which corresponded to a yield of 93%.

The compound obtained had the following formula:

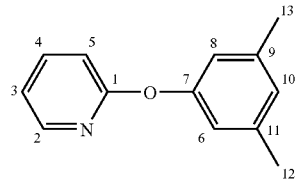

The characteristics were as follows:
$^1$H NMR/CDCl$_3$: δ 8.21 (ddd, 1H, $^3J_{HH}$=5.0 Hz, $^4J_{HH}$=2.0 Hz, $^5J_{HH}$=0.7 Hz, H$_2$), 7.66 (ddd, 1H, $^3J_{HH}$=8.2 Hz, $^3J_{HH}$=7.2 Hz, $^4J_{HH}$=2.0 Hz, H$_4$),6.97 (ddd, 1H$^{13}J_{HH}$=7.2 Hz, $^3J_{HH}$=5.0 Hz, $^4J_{HH}$=0.9 Hz, H$_3$), 6.88 (ddd, 1H, $^3J_{HH}$=8.2 Hz, $^4J_{HH}$=0.9 Hz, $^5J_{HH}$=0.7 Hz, H$_5$), 6.84 (m, 1H, H$_{10}$), 6.76 (m, 2H, H$_{6,8}$), 2.32 (s, 6H, H$_{12,13}$);
$^{13}$C NMR/CDCl$_3$: δ 164.02 (C1), 154.15 (C7), 147.87 (C2), 139.47 (C9 and C11), 139.27 (C4), 126.53 (C10), 118.80 (C6 and C8), 118.22 (C5), 111.47 (C3), 21.34 (C12 and C13);
Elemental analysis: Calculated: C: 78.21%; H: 6.69%; N: 7.04%. Found C: 78.36%; H: 6.58%; N: 7.03%;
GC/MS: Rt=17.65 min, M/Z=199, purity=99%;
IR (CH$_2$Cl$_2$): 3027 (VW, aromatic), 1468 and 1430 (VW, aromatic C═C), 1220 (S, C—O), 781 (S), 759 (VS), 751 (S);
Rf: 0.22 (eluent: hexane/dichloromethane, 75/25).

Example 4

Arylation of Carbon-containing Nucleophiles

Example 4.1

Synthesis of Diethyl 2-phenylmalonate 38 mg of cuprous iodide (0.2 mmoles), 117 mg of Chxn-Py-Al (0.4 mmoles) and 977 mg of caesium carbonate (3 mmoles) were successively introduced into a 35 ml Schlenk tube that had been oven dried at 100° C. and provided with a magnetic stirrer (12×4.5 mm) and under a nitrogen atmosphere.
The Schlenk tube was purged under vacuum then refilled with nitrogen.
607 μl of diethyl malonate (3 mmoles), 224 μl of iodobenzene (2 mmoles), 1.2 ml of acetonitrile and 600 mg of ground and activated 3 Å molecular sieve were then added.
The reactor was placed in an oil bath at a temperature of 70° C. and stirred for a period of 30 hours.
A compound with the following formula was obtained:

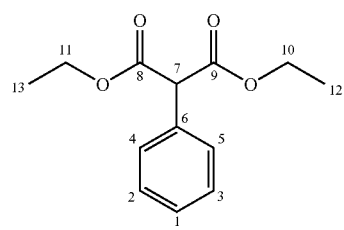

The characteristics were as follows:

$^1$H NMR/CDCl$_3$: δ 7.32–7.42 (m, 5H, H$_{15}$), 4.62 (s, 1H, H$_7$), 4.22 (m, 4H, H$_{10,11}$), 1.26 (t, $^3J_{HH}$=7.1 Hz, 6H, H$_{12,13}$);

$^{13}$C NMR/CDCl$_3$: δ 168.15 (C8 and C9), 132.86 (C6), 129.27 (C2 and C3), 128.58 (C4 and C5), 128.18 (C1), 61.77 (C11 and C12), 58.00 (C7), 14.00 (C12 and C13);

GC/MS: Rt=16.77 min, M/Z=236, purity=99%;

Rf: 0.27 (eluent: hexane/dichloromethane, 70/30).

What is claimed is:

1. A process for N-arylating, or N-vinylating a nucleophilic compound consisting of a five membered heterocyclic ring containing nitrogen, selected from the group consisting of pyrrole, imidazole, pyrazole, triazole, indole, and tetrazole, comprising the steps of:

a) reacting the nucleophilic compound with a compound with a leaving group according to formula (IV):

R$_0$—Y  (IV)

wherein:

Y is a leaving group, and

R$_0$ represents a hydrocarbon group containing 2 to 20 carbon atoms having a double bond or a triple bond located in the position a to the leaving group Y, a monocyclic group, a polycyclic group, an aromatic group, a carbocyclic group, or a heterocyclic group, wherein the reaction is carried out in the presence of a catalytically effective amount of a catalyst comprising:

a metallic element M selected from the group consisting of the elements of the groups (VIII), (Ib) and (IIb) of the periodic table, and at least one ligand comprising at least one imine group and at least one further nitrogen atom, as a chelating atom, selected from the following formulae Ia$_1$, Ia$_2$, Ib$_1$, Ib$_2$ and Ic$_1$:

(Ia$_1$)

(Ia$_2$)

wherein, one of the groups R$_a$ and R$_b$ optionally comprises at least one nitrogen atom or a group comprising a nitrogen atom, R$_a$ and R$_b$, which are identical or different, represent a hydrocarbon group containing 1 to 20 carbon atoms, said hydrocarbon group being:
a linear or branched, saturated or unsaturated, acyclic aliphatic group,
a saturated, unsaturated or aromatic, monocyclic or polycyclic, carbocyclic or heterocyclic, group, or
a concatenation thereof, R$_a$ and R$_b$ are optionally bonded to constitute, with a carbon atoms carrying them, a monocyclic or polycyclic, saturated or unsaturated, carbocyclic or heterocyclic, group containing 3 to 20 atoms, R$_c$ represents a hydrogen atom, an alkyl group, an alkenyl group, an alkynyl group, a cycloalkyl group, an aryl group, an arylalkyl group, an amido group —CO—NH$_2$, or an amido group substituted with one or two alkyl, alkenyl, alkynyl, cycloalkyl, aryl or arylalkyl group;

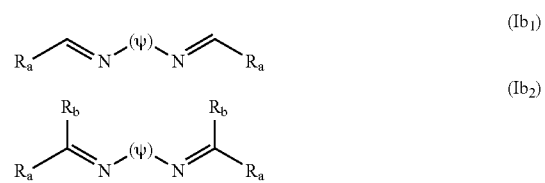

(Ib$_1$)

(Ib$_2$)

wherein:

R$_a$, which is identical or different, is as defined above,

R$_b$, which is identical or different, is as defined above, and

Ψ represents a group of formula —HN—CO—NH— or a skeleton having one of the following formulae (F$_2$) or (F$_3$):

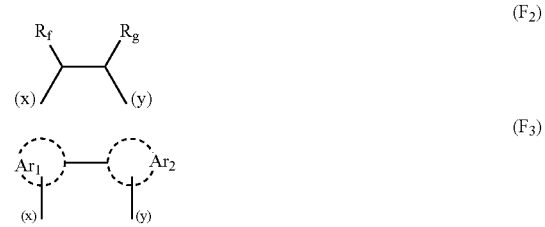

(F$_2$)

(F$_3$)

wherein:

R$_f$ and R$_g$, which are identical or different, represent a hydrocarbon group containing 1 to 20 carbon atoms, said hydrocarbon group being:
a linear or branched, saturated or unsaturated, acyclic aliphatic group,
a saturated, unsaturated or aromatic, monocyclic or polycyclic, carbocyclic or heterocyclic, group, or
a concatenation thereof, R$_f$ and R$_g$ are optionally bonded to constitute, with a carbon atoms carrying them, a monocyclic or polycyclic, saturated or unsaturated, carbocyclic or heterocyclic group containing 3 to 20 atoms, Ar$_1$ and Ar$_2$, which are identical or different, represent two substituted or non substituted aromatic, carbocyclic or heterocyclic cycles, optionally condensed, and optionally carrying one or more heteroatom, and x and y respectively represent the two bonds between the skeleton shown as ψ and the imine groups; and

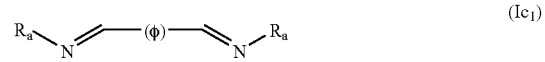

(Ic$_1$)

wherein:

R$_a$, which is identical or different, is as defined above, and

Φ represents:
a covalent bond,
an alkylene group having the following formula:

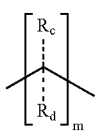

wherein m is equal to 0, 1 or 2, and $R_c$ and $R_d$, which are identical or different, represent:
a hydrogen atom,
a linear or branched alkyl group containing 1 to 12 carbon atoms, optionally carrying a halogen atom, or
a halogen atom, or
a residue of a monocyclic or polycyclic hydrocarbon cycle containing 5 to 12 carbon atoms carrying the two imine functions in the ortho or meta position; and
b) recovering the N-arylated or N-vinylated nucleophilic compound obtained in step a).

2. The process according to claim 1, wherein the ligand is a bidentate, tridentate or tetradentate ligand.

3. The process according to claim 1, wherein, in formulae $Ia_1$ and $Ia_2$, $R_c$ represents a $C_1$ to $C_{12}$ alkyl group, a $C_2$ to $C_{12}$ alkenyl group, a $C_2$ to $C_{12}$ alkynyl group, a $C_3$ to $C_{12}$ cycloalkyl group, a $C_6$ to $C_{12}$ aryl group, a $C_6$ to $C_{12}$ arylalkyl group, an amido group —CO—NH$_2$, or an amido group substituted with one or two $C_1$ to $C_{12}$ alkyl, $C_2$ to $C_{12}$ alkenyl, $C_2$ to $C_{12}$ ailcynyl, $C_3$ to $C_{12}$ cycloalkyl, $C_6$ to $C_{12}$ aryl or $C_6$ to $C_{12}$ arylalkyl group.

4. The process according to claim 1, wherein, in formulae $Ia_1$ and $Ia_2$, $R_c$, which is identical or different, represents a hydrogen atom or a methyl group, and $R_a$ represents a group selected from the group consisting of the groups having the following formulae:

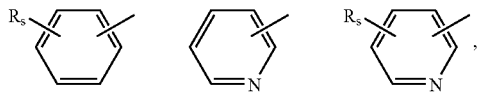

wherein $R_s$ represents an ailcyl group, an alkoxy group or an amino group optionally substituted with an alkyl group.

5. The process according to claim 4, wherein $R_s$ represents a $C_1$ to $C_4$ alkyl group, a $C_1$ to $C_4$ alkoxy group or an amino group optionally substituted with a $C_1$ to $C_4$ alkyl group.

6. The process according to claim 1, wherein, in formulae $(Ib_1)$ or $(Ib_2)$, the ligand has formula $(Ib_1)$ and $R_a$ represents a group selected from the group consisting of the groups having the following formulae:

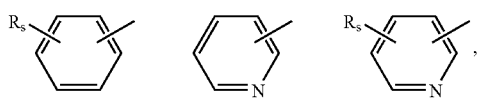

wherein $R_s$ represents an alkyl group, an alkoxy group or an amino group optionally substituted with an alkyl group.

7. The process according to claim 6, wherein $R_s$ represents a $C_1$ to $C_4$ alkyl group, a $C_1$ to $C_4$ alkoxy group or an amino group optionally substituted with a $C_1$ to $C_4$ ailcyl group.

8. The process according to claim 1, wherein, in formulae $(Ib_1)$ or $(Ib_2)$, Ψ represents a group selected from the group consisting of the cyclic groups having the following the following formulae:

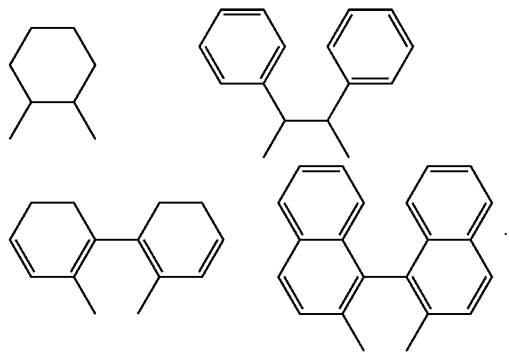

9. The process according to claim 1, wherein, in formula $(Ic_1)$, m is equal to 0 or 1, and $R_c$ and $R_d$, which are identical or different, represent:
a hydrogen atom,
a methyl, ethyl, propyl, isopropyl, butyl, isobutyl, sec-butyl or tert-butyl group, or
a halogen atom.

10. The process according to claim 1, wherein, in formula $(Ic_1)$, $R_a$, which is identical or different, represents a group selected from the group consisting of the groups having the following formulae:

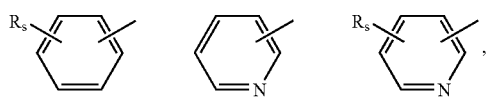

wherein $R_s$ represents an alkyl group, an alkoxy group or an amino group optionally substituted with an alkyl group.

11. The process according to claim 10, wherein $R_a$ represents a $C_1$ to $C_4$ alkyl group, a $C_1$ to $C_4$ alkoxy group or an amino group optionally substituted with a $C_1$ to $C_4$ alkyl group.

12. The process according to claim 1, wherein, in formula $(Ic_1)$, Φ represents a methylene or ethylene group, or a divalent cyclic group selected from the group consisting of the groups having the following the following formulae:

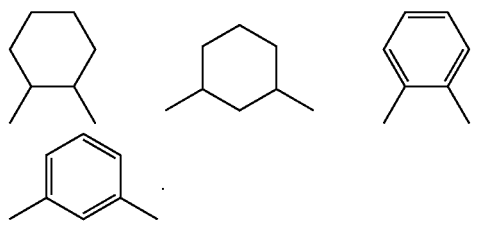

13. The process according to claim 1, wherein the ligand is selected from the group consisting of Ph-Alzone, Py-Aizone, N-Methyl-Py-Alzone, N-Dimethyl-Py-Alzone, N-Amido-Py-Alzone, Chxn-Phenyl-Al, Chxn-Py-Al, Carbo-Py-Al, Chxn-Thio-Al, and DAB-Cy.

14. The process according to claim 1, the amount of ligand is such that the ratio between the number of moles of ligand and the number of moles of metalisoffrom2to 1.

15. The process according to claim 1, wherein the nucleophilic compound comprises at least one nitrogen atom carrying a free electron pair included in said five membered heterocyclic ring.

16. The process according to claim 1, wherein the nucleophilic compound has the following formula (IIIh):

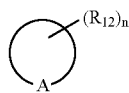
(IIIh)

wherein:
A represents the five membered heterocyclic ring,
$R_{12}$, which is be identical or different, represents a substituent on the ring, and
n represents the number of substituents on the ring.

17. The process according to claim 1, wherein:
$R_0$ represents:
an aliphatic hydrocarbon group containing a double bond or a triple bond in the position α to the leaving group Y, or a cyclic hydrocarbon group containing an unsaturated bond carrying a leaving group, or
a monocyclic or polycyclic, carbocyclic or heterocyclic, aromatic group, and
Y represents a leaving group being a halogen atom or a sulphonic ester group having the following formula —$OSO_2$—$R_e$, wherein $R_e$ is a hydrocarbon group.

18. The process according to claim 1, wherein
Y represents a bromine or chlorine atom or a sulphonic ester group having the following formula —$OSO_2$—$R_e$, wherein $R_e$ is a linear or branched alkyl group containing 1 to 4 carbon atoms, a phenyl group, a tolyl group or a trifluoromethyl group.

19. The process according to claim 1, wherein the compound with a leaving group is selected from the group consisting of the following compounds:
(1) aliphatic compounds having a double bond and having the following formula (IVa):

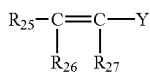
(IVa)

wherein
$R_{25}$, $R_{26}$ and $R_{27}$, which are identical or different, represent a hydrogen atom or a hydrocarbon group containing 1 to 20 carbon atoms, being:
a linear or branched, saturated or unsaturated, aliphatic group,
a monocyclic or polycyclic, saturated, unsaturated or aromatic, carbocyclic or heterocyclic, group,
or a concatenation of aliphatic, carbocyclic or heterocyclic, groups as defined above, and
Y represents the leaving group,
(2) aliphatic compounds having a triple bond, and having the following formula (IVb):

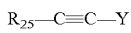 (IVb), wherein
$R_{25}$ has the meaning given above, and
Y represents the leaving group as defined above, and (3) aromatic compounds having the following formula (IVc):

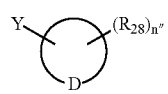
(IVc)

wherein:
D represents a residue of a cycle forming all or a portion of a monocyclic or polycyclic, carbocyclic or heterocyclic, aromatic system,
$R_{28}$, which is identical or different, represents a substituent on the cycle,
Y represents the leaving group, and
n" represents the number of substituents on the cycle.

20. The process according to claim 1, wherein the compound with a leaving group is vinyl chloride, vinyl bromide, bromoalkyne, iodoalkyne, β-bromostyrene, β-chlorostyrene, p-chlorotoluene, p-bromoanisole or p-bromotrifluorobenzene.

21. The process according to claim 1, wherein the catalyst comprises at least one metallic element M selected from the group consisting of copper, silver, palladium, cobalt, nickel, iron and zinc.

22. The process according to claim 21, wherein the catalyst is a copper halide catalyst.

23. The process according to claim 1, wherein the reaction is carried out in the presence of a base.

24. The process according to claim 23, wherein the base is:
an alkali metal carbonate, bicarbonate or hydroxide,
an alkaline-earth metal carbonate, bicarbonate or hydroxide,
an alkali metal hydride,
an alkali metal alcoholate, or
a tertiary amine.

25. The process according to claim 24, wherein the base is:
sodium, potassium or caesium carbonate, bicarbonate or hydroxide,
an calcium, barium or magnesium carbonate, bicarbonate or hydroxide,
sodium hydride, or
sodium methylate, ethylate or tertiobutylate.

26. The process according to claim 1, wherein the reaction is carried out in the presence of an organic solvent.

27. The process according to claim 26, wherein the organic solvent is:
a linear or cyclic carboxamide,
dimethylsulphoxide (DMSO),
hexamethylphosphotriamide (HMPT),
tetramethylurea,
a nitro compound,
an aliphatic or aromatic nitrile,
an organic carbonate,
an alkyl ester,
a halogenated aromatic hydrocarbon,
or a nitrogen-containing heterocycle.

28. The process according to claim 27, wherein the organic solvent is acetonitrile, tetramethylene sulphone, chlorobenzene, toluene, pyridine, picoline or a quinoline.

29. The process according to claim 1, wherein the reaction is carried out at a temperature of from 0° C. to 120° C.

30. The process according to claim 29, wherein the temperature is of from 25° C. to 85° C.

* * * * *